(12) United States Patent
Collazo et al.

(10) Patent No.: US 9,795,397 B2
(45) Date of Patent: Oct. 24, 2017

(54) ANATOMICALLY GUIDED INSTRUMENTATION FOR TROCHLEAR GROOVE REPLACEMENT

(71) Applicant: Stryker Corporation, Kalamazoo, MI (US)

(72) Inventors: Carlos E. Collazo, Old Greenwich, CT (US); Stuart L. Axelson, Jr., Austin, TX (US); Michael C. Ferko, Warwick, NY (US); Emily Hampp, Far Hills, NJ (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/137,391

(22) Filed: Apr. 25, 2016

(65) Prior Publication Data

US 2016/0235420 A1 Aug. 18, 2016

Related U.S. Application Data

(63) Continuation of application No. 14/188,915, filed on Feb. 25, 2014, now Pat. No. 9,358,117.

(Continued)

(51) Int. Cl.
*A61F 2/38* (2006.01)
*A61B 17/17* (2006.01)
(Continued)

(52) U.S. Cl.
CPC ........ *A61B 17/175* (2013.01); *A61B 17/1742* (2013.01); *A61B 17/1764* (2013.01);
(Continued)

(58) Field of Classification Search
CPC .......... A61F 2/3859; A61F 2/38; A61B 17/17; A61B 17/1728; A61B 17/1739
See application file for complete search history.

(56) References Cited

U.S. PATENT DOCUMENTS 5,593,450 A 1/1997 Scott et al.
7,608,079 B1 10/2009 Blackwell et al.
(Continued)

OTHER PUBLICATIONS

Partial International Search Report for Application No. PCT/US2014/018300 dated Jun. 10, 2014.
(Continued)

*Primary Examiner* — Jason-Dennis Stewart
(74) *Attorney, Agent, or Firm* — Lerner, David, Littenberg, Krumholz & Mentlik, LLP

(57) ABSTRACT

A system for replacing a trochlear groove region of a femur. The system includes a prosthesis that includes a bone contact surface and a periphery that defines an outer perimeter. The bone contact surface has a plurality of protrusions and a spatial configuration with respect to one another. Additionally, the system includes a first template that has a plurality of guide holes and a first periphery that defines an outer perimeter that substantially corresponds with the periphery of the prosthesis. Also, included in the system is a second template that has a plurality of guide holes and a second periphery that defines an outer perimeter that substantially corresponds with the periphery of the prosthesis. The plurality of guide holes of the second template are spatially arranged with respect to the second periphery to substantially match the spatial configuration of the plurality of protrusions of the prosthesis.

10 Claims, 50 Drawing Sheets

Related U.S. Application Data

(60) Provisional application No. 61/768,765, filed on Feb. 25, 2013.

(51) Int. Cl.
*A61F 2/30* (2006.01)
*A61B 17/15* (2006.01)
*A61B 17/16* (2006.01)

(52) U.S. Cl.
CPC .......... *A61F 2/3859* (2013.01); *A61F 2/3877* (2013.01); *A61B 17/155* (2013.01); *A61B 17/1604* (2013.01); *A61B 17/1675* (2013.01); *A61F 2002/30878* (2013.01)

(56) References Cited

U.S. PATENT DOCUMENTS

| | | |
|---|---|---|
| 8,419,741 B2 | 4/2013 | Carignan et al. |
| 8,523,869 B2 | 9/2013 | Scifert et al. |
| 2003/0120346 A1 | 6/2003 | Mercinek et al. |
| 2005/0119664 A1 | 6/2005 | Carignan et al. |
| 2007/0288021 A1 | 12/2007 | Rickels et al. |
| 2008/0281329 A1 | 11/2008 | Fitz et al. |
| 2009/0216285 A1 | 8/2009 | Ek et al. |
| 2009/0281583 A1 | 11/2009 | Brown et al. |
| 2010/0036383 A1 | 2/2010 | Major et al. |
| 2010/0036444 A1 | 2/2010 | Major et al. |
| 2010/0094429 A1 | 4/2010 | Otto |
| 2010/0222781 A1 | 9/2010 | Collazo et al. |
| 2010/0222782 A1 | 9/2010 | Collazo et al. |
| 2011/0264097 A1 | 10/2011 | Hodorek et al. |
| 2011/0295375 A1 | 12/2011 | Appenzeller et al. |
| 2012/0259335 A1 | 10/2012 | Scifert et al. |
| 2013/0204259 A1 | 8/2013 | Zajac |
| 2015/0182237 A1 | 7/2015 | Nadzadi et al. |

OTHER PUBLICATIONS

International Search Report and Written Opinion for Application No. PCT/US2014/018300 dated Jul. 22, 2014.

ANATOMICALLY GUIDED INSTRUMENTATION FOR TROCHLEAR GROOVE REPLACEMENT

CROSS-REFERENCE TO RELATED APPLICATIONS

This application is a continuation of U.S. application Ser. No. 14/188,915, filed on Feb. 25, 2014, which claims the benefit of the filing date of U.S. Provisional Patent Application No. 61/768,765 filed Feb. 25, 2013, all of which are hereby incorporated herein by reference.

FIELD OF THE INVENTION

The present invention relates to systems and methods for use in patellofemoral knee replacement, and in particular, relates to positioning guides and bone preparation tools for preparation of the trochlear groove of a patient's femur and patellofemoral prostheses for implantation thereon.

BACKGROUND OF THE INVENTION

The knee joint is a tri-compartmental joint consisting of the medial and lateral compartments which make up the tibiofemoral joint ("TFJ") and the patellofemoral compartment which makes up the patellofemoral joint ("PFJ"). The PFJ more specifically includes the patella and the trochlear groove of the femur. Noninflamatory degenerative joint disease, such as osteoarthritis, inflammatory joint disease, such as rheumatoid arthritis, traumatic injuries and structural abnormalities may affect any combination of the aforementioned knee compartments. Severe pain may result where the articular cartilage of the patella and/or the femoral trochlear groove is eroded or otherwise damaged and natural motion of the patella along the trochlear groove is impeded. For patients with erosion or damage confined to the PFJ, or for patients with a history of chronic patella dislocations, a patellofemoral joint replacement may offer a beneficial alternative to total joint replacement. Moreover, a patellofemoral joint replacement generally provides pain relief or improved patella tracking while preserving significantly more bone than a total joint replacement.

In total joint replacement, all three compartments are effected whereby portions of a patient's trochlear groove, medial and lateral condyles, and tibial plateau are generally each resected and substituted for by one or more joint prostheses. In contrast, in PFJ replacement, generally only the patella and the trochlear groove are replaced. A major benefit of PFJ replacement over total joint replacement is bone preservation, which may reduce recovery time and post-operative pain. Another advantage of bone preservation is that the joint line may be maintained resulting in a more normal functioning knee. Further advantages may include less cost and procedure duration, which reduces the likelihood of contracting an infection and positively affects recovery time.

Current PFJ replacement systems employ several types of instruments for removing bone in the trochlear groove region of the femur. For example, forming bone adjacent the intercondylar notch of the trochlear groove may occur with a rongeur, osteotome, rasp, reciprocating or oscillating saw, burr, or a combination of all of these instruments. However, a common characteristic of the use of these instruments in current PFJ replacement is that they are generally free-hand instruments that primarily rely on the skill of the surgeon handling them. However, even a skilled surgeon may have trouble duplicating results where speed and precision are critical. Therefore, one of the biggest drawbacks of current instrumentation is that each provides no true anatomically based means for guiding the surgeon to restore the trochlear groove or patellar track to ensure proper patellofemoral kinematics. Further, certain existing patellofemoral implants have asymmetric designs and few sizing options, which frequently results in a poor anatomic fit. Guided formation of this bone and proper selection of patellofemoral implants are important for implant stability and sustainability, as well as assuring natural patellar tracking and restoration of the "Q angle" defined by the lines representing the pull of the quadriceps muscle on the patella and the axis formed by the patella tendon between the patella and tibial tubercle.

Therefore, there is a need for guided PFJ reconstruction instrumentation that provides accurate, reproducible results and a varied selection of anatomic patellofemoral implantation with improved patellar tracking characteristics that collectively provide added natural post-operative knee kinematics.

BRIEF SUMMARY OF THE INVENTION

According to a first aspect of the present invention, a prosthesis for implantation within a prepared trochlear groove of a femur bone is disclosed herein. The prosthesis includes a proximal region that has a first bone contact surface. The first bone contact surface has a plurality of protrusions that extend outwardly therefrom for insertion into a plurality of bone voids formed in the femur bone. The plurality of protrusions each have a longitudinal axis that is acutely angled to a plane of the first bone contact surface. The prosthesis further includes a distal region that includes a second bone contact surface. The second bone contact surface has an annulus projecting outwardly therefrom for insertion into a bone void formed in the femur bone. The annulus has a longitudinal axis that is perpendicular to a plane of the second bone contact surface, wherein the plane of the first bone contact surface is angled with respect to the plane of the second bone contact surface.

According to one embodiment of this first aspect, the annulus may be realized in the form of a sidewall defining a cavity therein. The sidewall may include at least one cut-out about the circumference of the sidewall such that cut-out may be in fluid communication with the cavity.

According to another embodiment of the first aspect, the at least one cut-out may be realized in the form of a plurality of cut-outs that are arranged in a radial array about the circumference of the sidewall of the annulus.

According to yet another embodiment of this first aspect, the implant may include an articular surface opposite the first and second bone contact surfaces. The articular surface may include a medial and a lateral portion, wherein the lateral portion of the articular surface has a wider profile than the medial portion of the articular surface.

According to a second aspect of the present invention is a system for replacing a trochlear groove region of a femur bone. The system includes a prosthesis that includes a bone contact surface and a periphery that defines an outer perimeter of the bone contact surface. The bone contact surface has a plurality of protrusions for insertion into the femur bone. The plurality of protrusions have a spatial configuration with respect to one another.

Additionally, the system includes a first template that has a plurality of guide holes. Further, the first template has a first periphery that defines an outer perimeter of the first template that substantially corresponds with the periphery of the prosthesis. Also, included in the system is a second template that has a plurality of guide holes. Furthermore, the second template has a second periphery that defines an outer perimeter of the second template that substantially corresponds with the periphery of the prosthesis. The plurality of guide holes of the second template are spatially arranged with respect to the second periphery to substantially match the spatial configuration of the plurality of protrusions of the prosthesis.

In one embodiment, the bone contact surface of the prosthesis may include a proximal region and a distal region. The plurality of protrusions may be at least two protrusions extending from the proximal region of the bone contact surface and one protrusion extending from the distal surface. The at least two protrusions may be realized in the form of pegs and the one protrusion may be realized in the form of an annulus having a sidewall, which defines a cavity therein.

The sidewall may include at least one cut-out about the circumference of the sidewall such that the cut-out is in fluid communication with the cavity. The at least one cut-out may be realized in the form of a plurality of cut-outs that are arranged in a radial array about the circumference of the sidewall of the annulus.

In another embodiment, the first template may further include a proximal region and a distal region that extends from the proximal region. The proximal region may have a flat bone engaging surface that includes a plane configured to substantially mate a plane of a resected portion of the femur bone. Further, the proximal region of the first template may include a window to view the resected portion of the femur bone therethrough when the flat bone engaging surface substantially mates to the resected portion of the femur bone.

Yet another embodiment, the least one of the plurality of guide holes of the first template is located in the proximal region, and at least one of the plurality of guide holes of the first template is located in the distal region.

Further, the distal region may be arcuate and taper distally from the proximal region and terminate at the periphery of the first template.

According to a third aspect of the present invention is a system for replacing a trochlear groove region of a femur bone. The system includes a prosthesis that has a bone contact surface and a periphery defining an outer perimeter of the bone contact surface. The bone contact surface has a plurality of protrusions for insertion into the femur bone. The plurality of protrusions have a spatial configuration with respect to one another. Additionally, the system includes a first template that has a guide opening and a first periphery that defines an outer perimeter of the first template that substantially corresponds with the periphery of the prosthesis. The guide opening is configured to receive and guide a bone punch instrument. Also included in the system is a second template that has at least one guide hole and a second periphery that defines an outer perimeter of the second template and that substantially corresponds with the periphery of the prosthesis. The at least one guide hole is configured to receive a bone resection tool.

In one embodiment, the bone contact surface of the prosthesis includes a proximal region and a distal region. The plurality of protrusions may be at least two protrusions extending from the proximal region of the bone contact surface and one protrusion extending from the distal region of the bone contact surface. The at least two protrusions may be realized in the form of pegs and the one protrusion may be realized in the form of an annulus that has a sidewall, which defines a cavity therein.

The sidewall may include at least one cut-out about the circumference of the sidewall such that the cut-out is in fluid communication with the cavity. The at least one cut-out may be realized in the form of a plurality of cut-outs that are arranged in a radial array about the circumference of the sidewall of the annulus.

In another embodiment, the first template may further include a proximal region and a distal region that extends from the proximal region. The proximal region may have a flat bone engaging surface that includes a plane configured to substantially mate a plane of a resected portion of the femur bone. Further, the proximal region of the first template may include a window to view the resected portion of the femur bone therethrough when the flat bone engaging surface substantially mates to the resected portion of the femur bone.

In yet another embodiment, the guide opening may be located in the distal region of the first template. The distal region may include a flange around the perimeter of the guide opening for smooth insertion of the bone punch instrument. Further, the flange may include a recess for receipt of depth stop tabs of the bone punch instrument.

BRIEF DESCRIPTION OF THE DRAWINGS

These and other features, aspects, and advantages of the present invention will become better understood with regard to the following description, appended claims, and accompanying drawings where:

DETAILED DESCRIPTION

As used herein, the term "proximal" means closer to the heart, and the term "distal" means further from the heart. The term "anterior" means toward the front part of the body or the face, and the term "posterior" means toward the back of the body. The term "medial" means toward the midline of the body, and the term "lateral" means away from the midline of the body. F/E refers to flexion and extension rotation about the epicondylar axis of a femur bone. I/E refers to internal and external rotation about the longitudinal axis of the intramedullary canal of a femur bone.

Figure 1A:
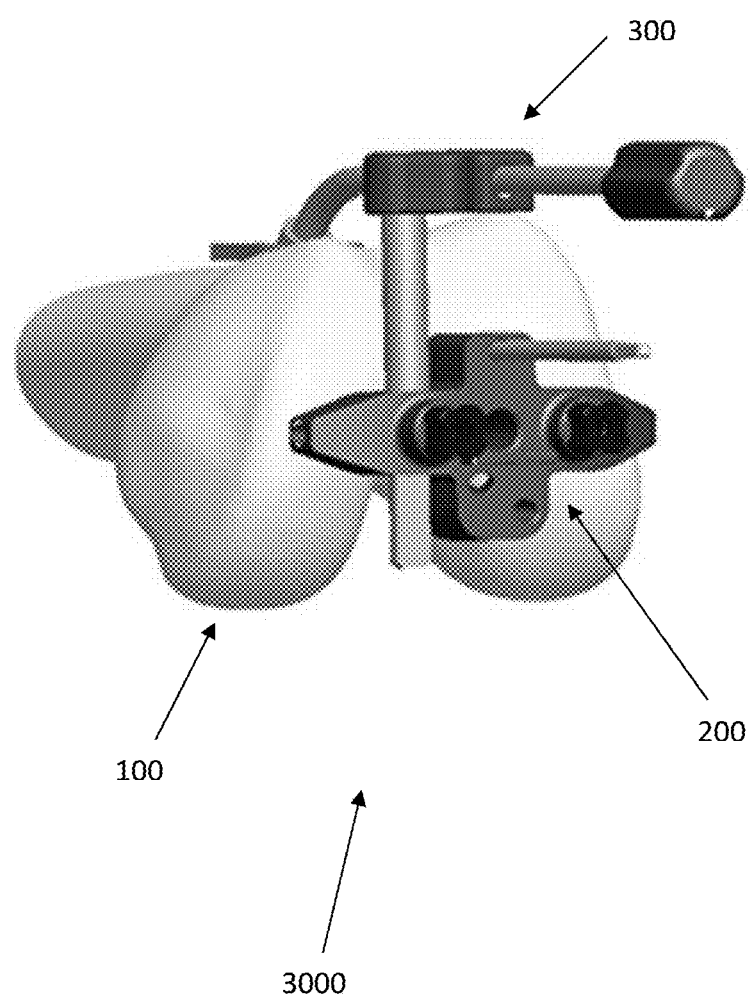
FIG. 1A shows a perspective view of a flexion/extension ("F/E") alignment assembly having an intercondylar block and an F/E stylus assembly.
Figure 1B:
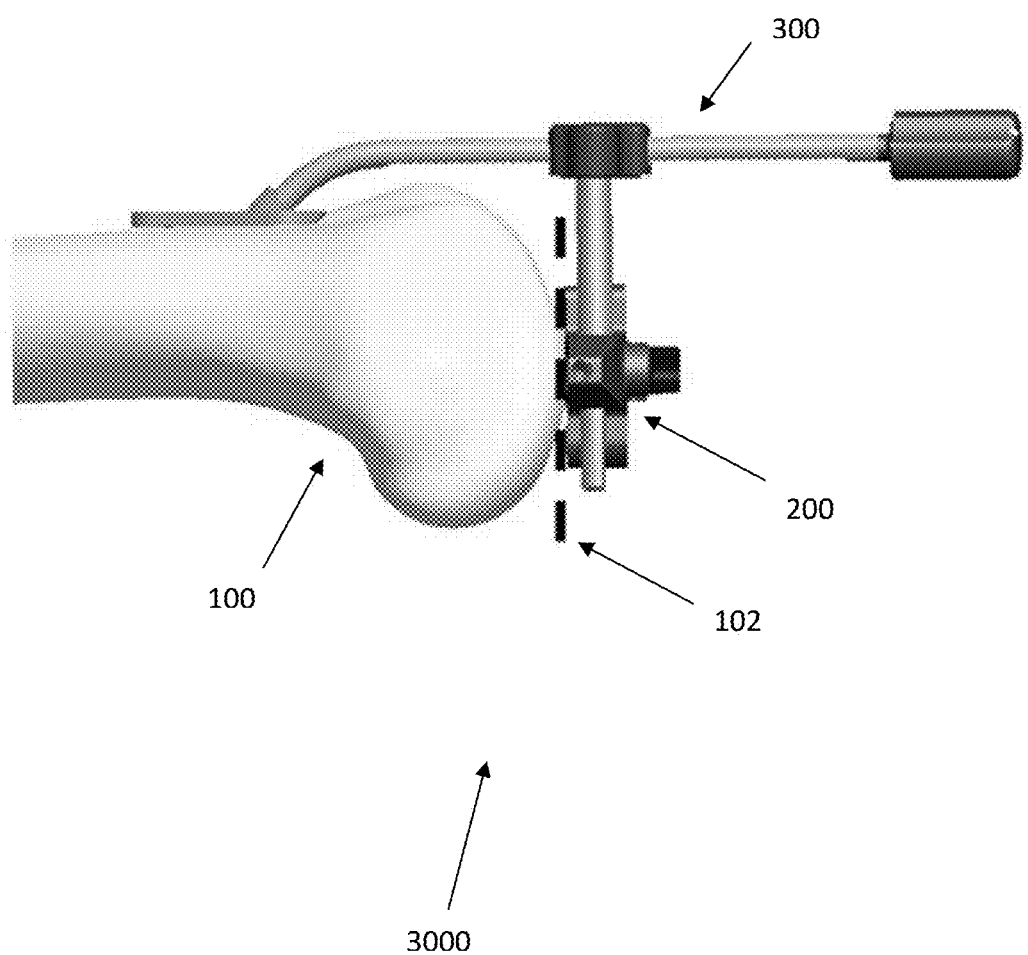
FIG. 1B shows a side view of the F/E alignment assembly of FIG. 1A.

FIGS. 1A and 1B show an F/E alignment assembly 3000 in accordance with an embodiment of the present invention. The F/E alignment assembly 3000 includes an F/E stylus assembly 300 and an intercondylar block 200.

Figure 2:
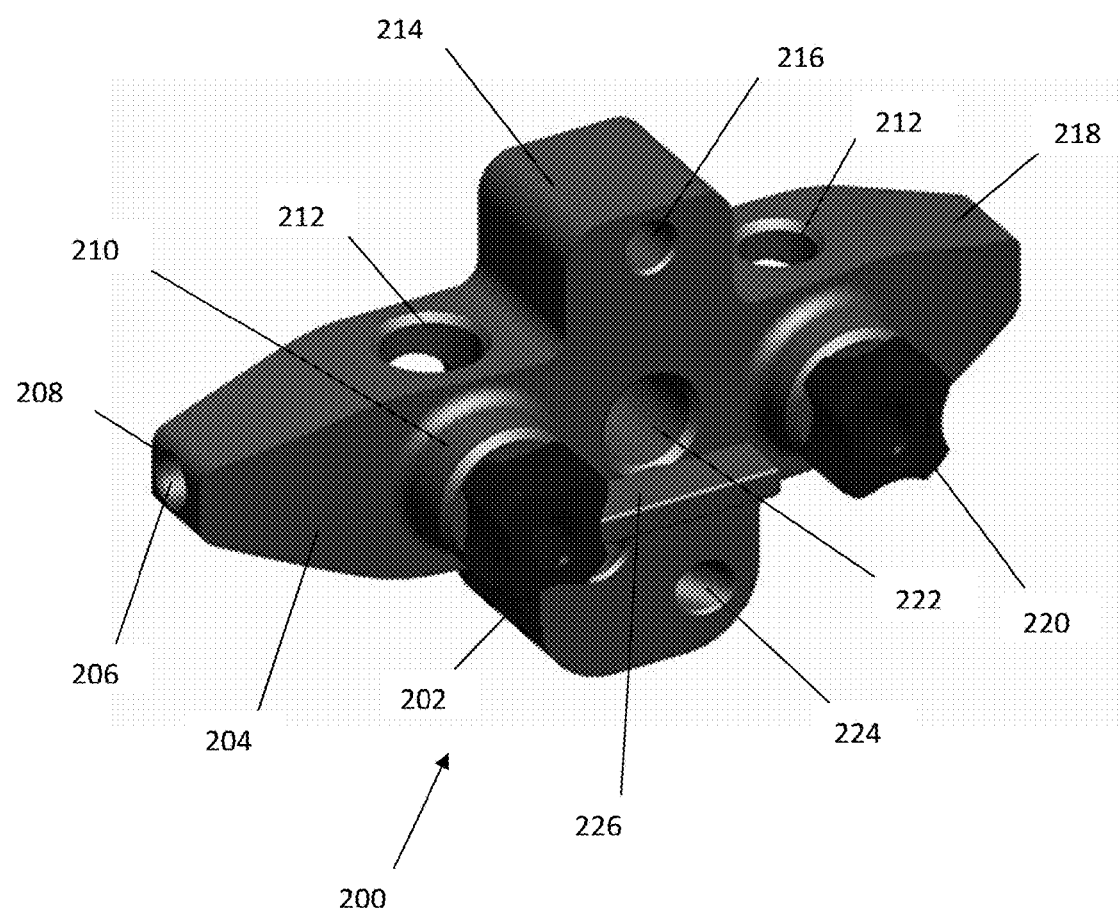
FIG. 2 shows a perspective view of the intercondylar block of FIG. 1A.

FIG. 2 shows the intercondylar block 200, which generally includes a lateral-medial ("L-M") member 204, an anterior-posterior ("A-P") member 214, and a plurality of holes. The plurality of holes includes a center alignment hole 222, cross pinholes 224, epi-alignment pinholes 206, bossed holes 210, flanking holes 212, and an overhead pinhole 216. In one embodiment, the intercondylar block 200 is generally cross shaped wherein the L-M member 204 orthogonally intersects the A-P member 214. The intercondylar block 200 also includes a bone interface surface and a distal surface that is opposite the bone interface surface and separated by the thickness of the intercondylar block. This thickness forms anterior 218, posterior 202, and L-M surfaces 208 that are generally perpendicular to the bone interface and distal surfaces. The locations where these surfaces intersect are preferably rounded to lessen the risk of soft tissue damage.

In one embodiment of the present invention there are two flanking holes 212 extending from the anterior surface 218 through the posterior surface 202 of the L-M member 204, with each of these flanking holes 212 situated on each side of the the A-P member 214. The distance of the longitudinal axis of the A-P member 214 to the center of one flanking hole 212 may be equal to the distance between the longitudinal axis of the A-P member 214 to the center of the other flanking hole 212. Each of the flanking holes 212 may be orthogonally intersected by a bossed hole 210. However, in other embodiments the flanking holes 212 may be angled. Each bossed hole 210 extends from the distal surface of the intercondylar block into a corresponding flanking hole 212, wherein the longitudinal axis of the flanking hole 212 preferably intersects with the longitudinal axis of the bossed hole 210. However, the bossed hole 210 preferably does not extend through the bone interface surface, but may extend through the bone interface surface in some embodiments. Each bossed hole 210 has a boss that extends distally from the distal surface. Additionally, each bossed hole may include a captured screw 220, which may be threaded to extend into and retract out of the flanking hole 212 when a torque is applied to the captured screw 220. The captured screw 220 preferably has a flat surface at the end of its shank in order to engage and hold a surface of an object inserted into the flanking hole 212. However, other embodiments may include surfaces of differing shapes, for example a conical point or a rounded edge.

Extending through each of the L-M surfaces 208 is an epi-alignment pinhole 206. The epi-alignment pinholes 206 preferably terminate prior to extension into a flanking hole 212. However, the longitudinal axis of each epi-alignment pinhole 206 preferably, orthogonally intersects the longitudinal axis of each flanking hole 212. However, other embodiments may provide for these axes to be offset from each other. Further, the longitudinal axis of the epi-alignment pinholes 206 are parallel and preferably collinear with the longitudinal axis of the L-M member 204.

Located generally at the center of rotation of the intercondylar block 200 is the center alignment hole 222, which extends from the distal surface and may either extend through the bone interface surface or terminate within the intercondylar block 200. An alignment platform 226 resides on the distal surface adjacent to the center alignment hole 222. The alignment platform 226 has an upper surface that is preferably parallel to a tangent line of the center alignment hole 222.

Located in an adjacent end of the A-P member 214 is an overhead pinhole 216, which extends from the distal surface through the bone interface surface. Located adjacent the opposite end of the A-P member 214 are two cross pinholes 224 that extend through the distal surface and may be offset from the longitudinal axis of the vertical member. The two cross pinholes 224 penetrate the intercondylar block 200 at an oblique angle with respect to the distal and bone contacting surfaces. The cross pinholes crisscross each other, but preferably do not intersect.

Figure 3:
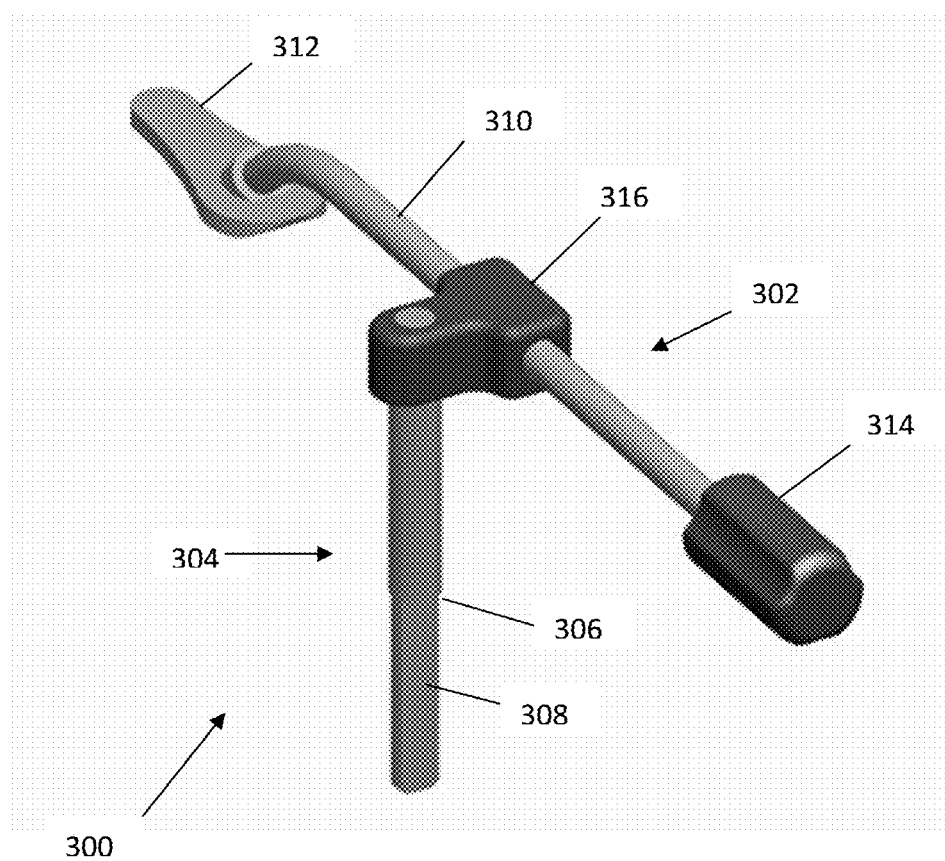
FIG. 3 shows a perspective view of the F/E stylus assembly of FIG. 1A.

Referring to FIG. 3, an F/E stylus assembly 300 is shown including a shouldered shaft 304, a housing 316, and an F/E stylus 302. The shouldered shaft may have a portion that is cylindrical and a portion that is semi-cylindrical, wherein these portions connect at a shoulder 306. The semi-cylindrical portion may have a flattened surface 308 that extends the length of the semi-cylindrical portion. The cylindrical portion has a larger radius than the semi-cylindrical portion. This difference in radii forms the shoulder 306. One end of the cylindrical portion is rigidly disposed within the housing 316.

The F/E stylus 302 has an F/E stylus shaft 310 which is rotationally and slidably disposed within the housing 316 such that the longitudinal axis of the F/E stylus shaft 310 is perpendicular to the longitudinal axis of the shouldered shaft 304. This slidability and rotatability is regulated by a leaf spring that resides in the housing 316, which provides resistance until a releasing force is achieved. Once the releasing force is achieved, the F/E stylus shaft 310 may move translationally or rotationally until the force is removed, thus reengaging the resistive force of the leaf spring. At one end of the F/E stylus shaft 310 is a handle 314, which is generally threaded onto shaft 310. The handle 314 allows the surgeon to rotate shaft 310 about its longitudinal axis for ease of removal from an incision, and improves the surgeon's grip via an ergonomic design that has enhanced frictional properties. The other end of the F/E stylus shaft 310 includes an alignment rudder 312. The alignment rudder has a bone contacting surface that is preferably angled at approximately 90 degrees with respect to the longitudinal axis of the shouldered shaft. In other embodiments, this angle could range from 86 to 90 degrees. The alignment rudder 312 is preferably elongated and flat to obtain a more accurate assessment of the planarity of the anterior cortex of the femur bone 100. In one embodiment, the bone contacting surface of the alignment rudder 312 may be rounded. In the embodiment illustrated by FIG. 3, the alignment rudder 312 is fixed to the F/E stylus shaft 310. However, in other embodiments the rudder 312 may rotate about its longitudinal axis.

Referring to FIGS. 1A and 1B, the shouldered shaft 304 is inserted into the either of the flanking holes 212 such that the F/E stylus shaft 310 is centered over the intercondylar block and orthogonal with the longitudinal axis of the A-P member 214. Thus, the housing 316 spaces the longitudinal axis of the shouldered shaft 304 from the longitudinal axis of the F/E stylus shaft 310 at the same distance as the longitudinal axis of the flanking holes 212 from the longitudinal axis of the A-P member 214. The shouldered shaft 304 is inserted into either of the flanking holes 212 wherein the shoulder 306 ensures the intercondylar block is not sitting too far anteriorly. Removal of the shouldered shaft 304 is prohibited by tightening the captured screw 220 that intersects the corresponding flanking hole 212 within which the shouldered shaft 304 is inserted. The flattened surface 308 of the shouldered shaft 304 and the flat surface of the end of the captured screw 220 engage to provide a solid lock and further ensures the F/E stylus shaft 310 is in proper geometric alignment with the intercondylar block 200.

FIGS. 1A and 1B also show an F/E alignment step in a patellofemoral arthroplasty. This step aligns the bone interface surface of the intercondylar block 200 with a distal plane 102 formed by the distal femoral condyles of the femur bone 100 and locks this alignment from further F/E rotation. Alignment is achieved by placing the bone contacting surface of the alignment rudder 312 in planar contact with the anterior cortex just proximal of the trochlear groove of the femur bone 100. The bone interface surface of the intercondylar block 200 is then moved into planar engagement with the distal plane 102 of the distal femoral condyles by sliding the housing 316 proximally on the F/E stylus shaft 310 until abutment occurs. The 90 degree angle of the alignment rudder 312, the planar reference of the anterior cortex, and the 90 degree angle between the F/E stylus shaft 310 and the shouldered shaft 304 ensures that the bone interface surface of the intercondylar block 200 is planar with the distal plane 102 of the distal femoral condyles. In other words, the 87 degree angle of the alignment rudder 304 along with other geometry of the F/E alignment assembly 3000 corresponds with the geometry of a femur bone 100 to confirm distal planar engagement. Further, the geometric location of the shoulder 306 on the shouldered shaft 304 and the geometry of the housing 316 and F/E stylus 302 is such that the intercondylar block 200 is precisely situated on the distal femoral condyles anteriorly-posteriorly in order to provide future anatomical reference by other surgical instrumentation in additional bone preparation steps. Thus, when the intercondylar block 200 is aligned with the distal plane 102 and the alignment rudder 304 is properly located on the anterior cortex, the proper anatomical height alignment is achieved. Alignment medially-laterally is at the surgeon's discretion, but the F/E stylus shaft 310 is generally centered over the trochlear groove. Once the proper alignment is achieved, a retainment pin 104 may be driven into the overhead pinhole 216 to lock F/E rotation of the intercondylar block 200. The F/E stylus assembly 300 is then removed from the intercondylar block 200 in preparation for an I/E alignment step.

Figure 4:
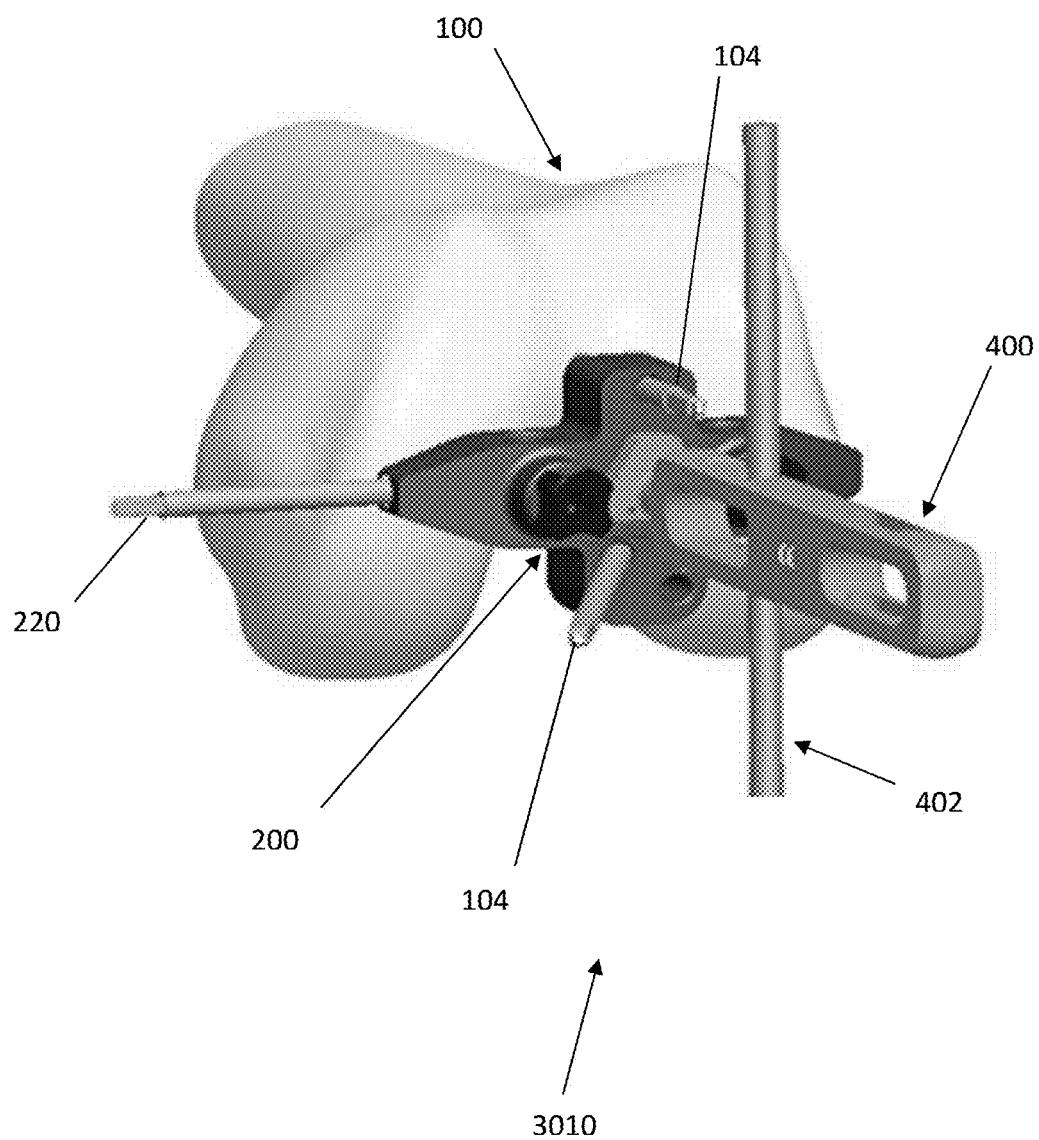
FIG. 4 shows a perspective view of an internal/external ("I/E") alignment assembly having the intercondylar block of FIG. 1A and an alignment handle.

FIG. 4 shows an I/E alignment assembly 3010 in accordance with an embodiment of the present invention. The I/E alignment assembly 3010 includes intercondylar block 200, epi-alignment pins 220, an alignment handle 400, and, optionally, a drop rod 402.

The alignment handle 400 generally has a handle portion that is rectangular and one end that includes a cylindrical portion for mating with the center alignment hole 222 and a triangular portion for mating with the alignment platform 226. A through-hole may extend through the handle portion to receive a drop rod.

With the intercondylar block 200 coupled with the distal femoral condyles via retainment pin 104 inserted into the overhead pinhole 216, an epi-alignment pins 220 is inserted into an epi-alignment pinhole 206 and the alignment handle 400 is inserted into the center alignment hole 222. The epi-alignment pins 220 are elongated such that they extend beyond the femur bone's periphery when inserted into the intercondylar block 200. The epi-alignment pin 220 is preferably inserted medially to reference the medial epicondyle. However, the surgeon may choose to align with the epi-alignment pins 220 laterally or both laterally and medially. The alignment handle 400 has a cylindrical portion at one end of the handle, which is inserted into the alignment center hole 222. Adjacent to the cylindrical portion, is a triangular portion that is generally an equilateral triangle. When the cylindrical portion is inserted into the center alignment hole 222, one of the sides of the triangular portion engages the alignment platform 226. A drop rod 402 may be inserted through the alignment handle 400 in parallel alignment with the longitudinal axis of the A-P member 214 of the intercondylar block 200.

Once the I/E alignment assembly is brought together, an I/E alignment step may be performed. In one embodiment, the surgeon rotates the intercondylar block 200 about the retainment pin 104 located in the overhead pinhole 216 by applying a torque to the alignment handle 400. Proper alignment is achieved when the epi-alignment pin 220 is visually aligned with the epicondylar axis. Alternatively, alignment may be achieved when the drop rod 402 visually aligns with a tibial reference of the surgeon's preference. This reference may be the tibial shaft, medial malleolus or Whiteside's line of the femur bone 100. Once the appropriate positioning is achieved, the surgeon locks further I/E rotation of the intercondylar block 200 by inserting a retainment pin 104 through either one or both cross pinholes 224. The angle of the cross pinholes 224 provides added stability of the intercondylar block 200 by, not only prohibiting I/E rotational movement, but also prohibiting lift-off of the intercondylar block 200 from the distal femoral condyles. Also, the angle of the cross pinholes 224 is optimized to allow the retainment pin 104 to enter into the intercondylar portion of the femur bone 100 in order to avoid damaging the articular surfaces of the femur bone 100 and avoid ligaments. Once alignment and locking is achieved, the epi-alignment pin 220 and alignment handle may be removed in preparation for resection height alignment.

Figure 5:
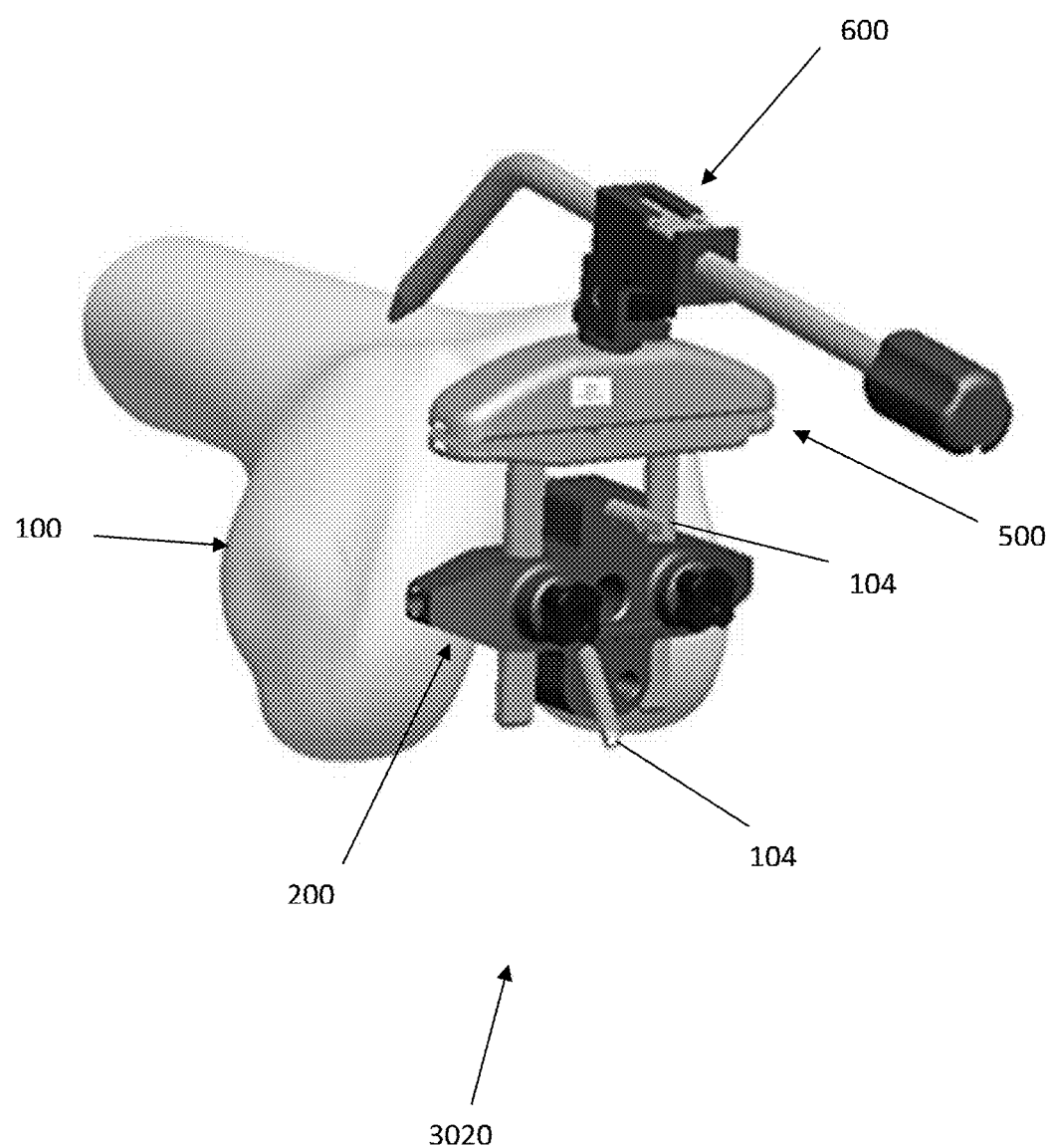
FIG. 5 shows a perspective view of an embodiment of a resection alignment assembly having the intercondylar block of FIG. 1A, a resection guide, and a resection stylus assembly.

FIG. 5 shows a resection alignment assembly 3020 in accordance with an embodiment of the present invention. The resection alignment assembly includes intercondylar block 200, a resection guide 500, and a resection stylus assembly 600.

Figure 6:
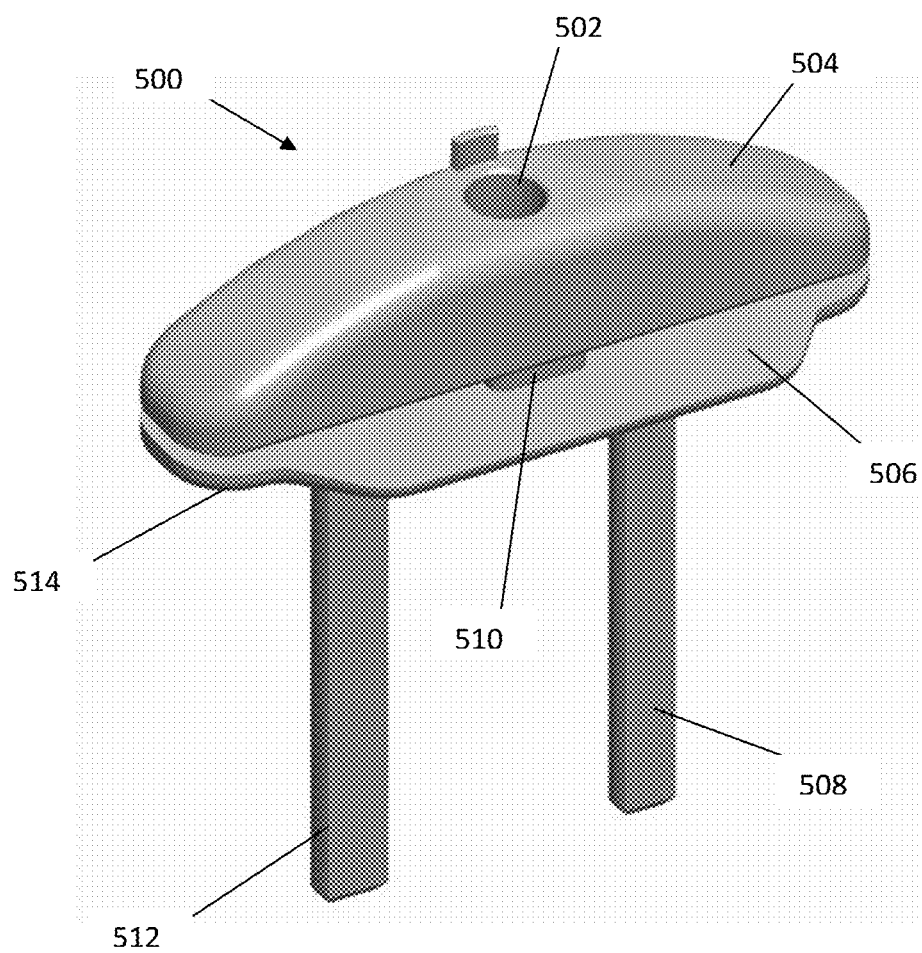
FIG. 6 shows a perspective view of the resection guide of FIG. 5.

FIG. 6 shows an embodiment of the resection guide 500. The resection guide generally includes a restriction plate 504, a resection plate 514, and a pair of retainment posts 512. Further, the resection guide 500 may be provided in various sizes based on the size of corresponding patellofemoral implant. The retainment posts 512 may be semi-cylindrical and may have a flattened surface 508 that runs along the length of each retainment post 512. Each retainment post 512 is attached to a posterior side of the resection plate 514. The resection plate has an anterior resection surface 506 opposite the posterior side. The anterior resection surface 506 is substantially flat and preferably angled at 4 degrees with respect to the distal plane 102 of the distal femoral condyles when the resection plate 514 interfaces the intercondylar block 200. The anterior resection surface 506 may have an extended surface to minimize pivoting and allow for a more accurate cut. The restriction plate 504 may be attached to the resection plate 514 by a central post 510 that connects the anterior resection surface 506 to a posterior surface of the restriction plate 504. The central post 510 provides a gap between the restriction 514 and resection 504 plates to allow for a bone saw to pass through to the femur bone 100. The central post 510 may have a rounded triangular shape to facilitate cutting at sharper angles. In other embodiments, there may be two outer posts in lieu of a central post. The restriction plate 506 may have a quick connect port 502 that extends through an anterior side of the restriction plate 504, but generally does not extend all the way through the restriction plate 504, however, may extend through in certain embodiments.

Figure 7:
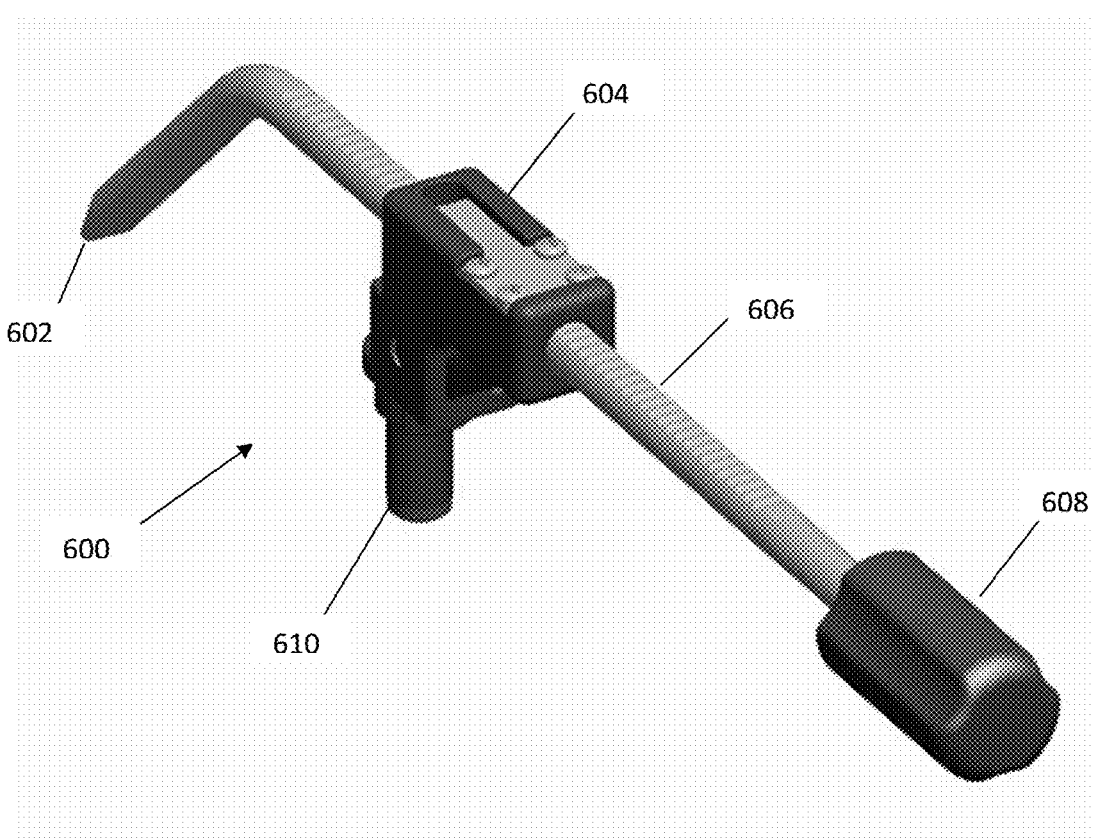
FIG. 7 shows a perspective view of the resection stylus assembly of FIG. 5.

FIG. 7 shows the resection stylus assembly 600. The restriction stylus assembly generally includes a quick connect mechanism 610, a housing 604 and a resection stylus rod 606. The resection stylus rod 606 is disposed rotationally and slidably within the housing 604. The slidability and rotatability of the resection stylus rod 606 is regulated by a leaf spring that resides in the housing 604, which provides resistance until a releasing force is achieved. Once the releasing force is achieved, the resection stylus rod 606 may move translationally or rotationally until the force is removed, thus reengaging the resistive force of the leaf spring. At one end of the resection stylus rod is a handle 608, which is generally threaded onto rod 606. The handle improves the surgeon's grip via an ergonomic design that has enhanced frictional properties. The other end of the resection guide rod 606 is bent and terminates with a stylus tip 602. The end of the stylus tip 602 is rounded and planar with the anterior resection surface 506 of the resection guide 500 when the resection stylus assembly 600 interfaces with the resection guide 500.

Also attached to the housing is the quick connect mechanism 610. Referring to FIG. 5, the quick connect mechanism is inserted into the quick connect port 502 of the resection guide 500. The quick connect mechanism 610 generally includes a spring-loaded device that engages the quick connect port 502 of the resection guide 500, thereby restricting removal of the resection stylus assembly 600 from the resection guide 500. However, the quick connect mechanism 610 allows for rotation within the quick connect port 502.

Once the resection stylus assembly 600 and resection guide 500 are joined, a resection height alignment step may be performed. The retainment posts 508 are inserted into the flanking holes 212 of the intercondylar block 200 such that the flattened surfaces 508 of the retainment posts 512 face the captured screws 220 and the stylus tip 602 of the resection stylus rod 606 points toward the anterior cortex of the femur bone 100. The surgeon may use the handle 608 to manipulate the stylus tip 602 by sliding and/or rotating the resection stylus rod 606 within the housing 604 and lifting or pressing down on the handle 608 to change the height position of the resection guide 500 with respect to the intercondylar block 200 until the runout of the stylus tip 602 interfaces with the lowest point of the proximal end of the trochlear groove of the femur bone 100. Once this is achieved, the dimensions between the stylus tip 602 and the longitudinal axis of the resection stylus rod 606 and between the longitudinal axis of the resection stylus rod 606 and the portion of the quick connect mechanism 610 that interfaces with the restriction plate 504 ensures that the anterior resection surface 514 is at the proper resection height. This resection height is set by locking down the captured screws 220, which locks the resection guide 500 at the proper resection height, thereby achieving proper height alignment.

Figure 8:
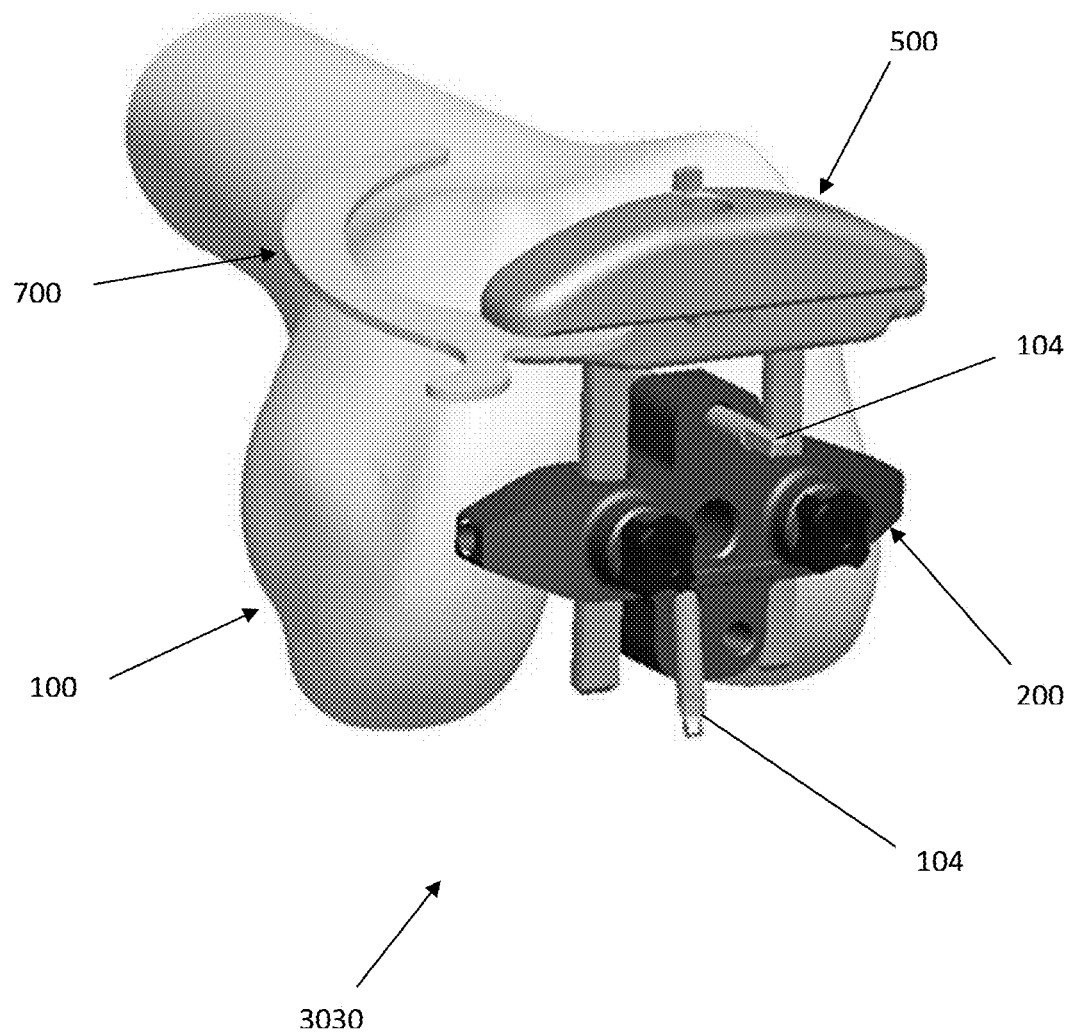
FIG. 8 shows a perspective view of a resection demonstration assembly having the intercondylar block of FIG. 1A, the resection guide of FIG. 5, and a blade runner.

The proper height alignment may be further verified by demonstrating the resection plane before cutting the femur bone 100. FIG. 8 shows an embodiment of a resection demonstration assembly 3030 according to the present invention. The resection demonstration assembly generally includes intercondylar block 200, resection guide 500, and a blade runner 700.

Figure 9:
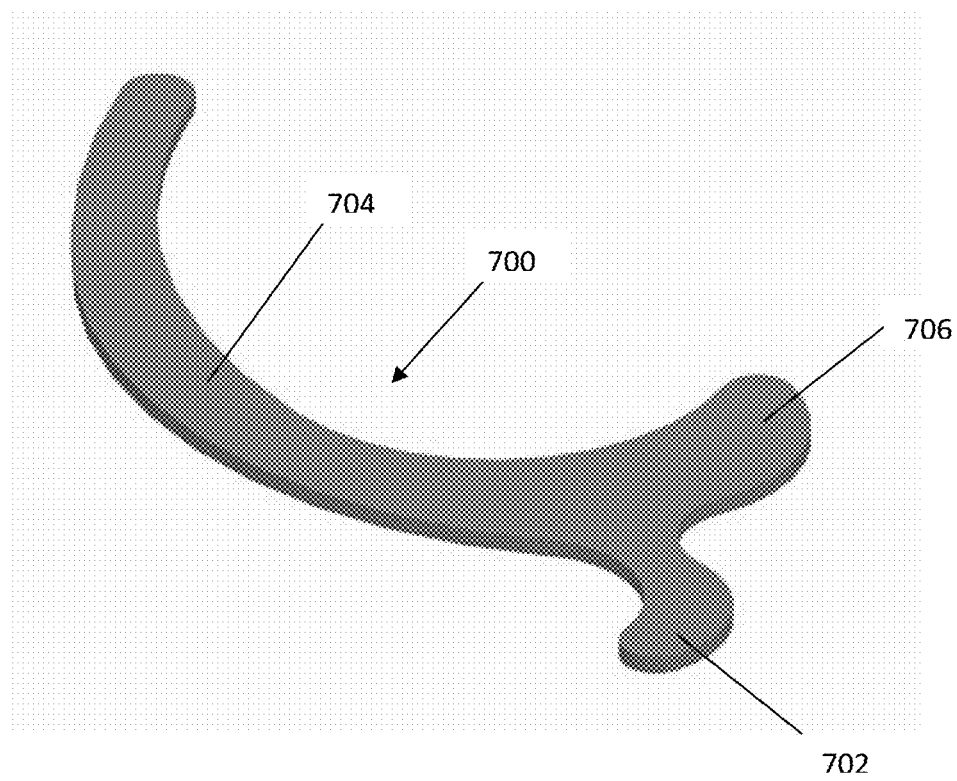
FIG. 9 shows a perspective view of the blade runner of FIG. 8.
Figure 10:
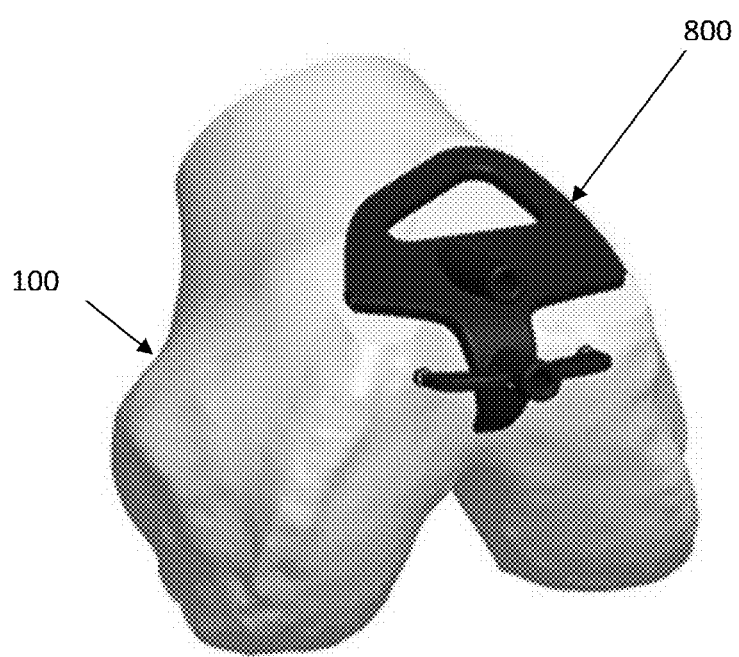
FIG. 10 shows a perspective view of an implant profiler.
Figure 11A:
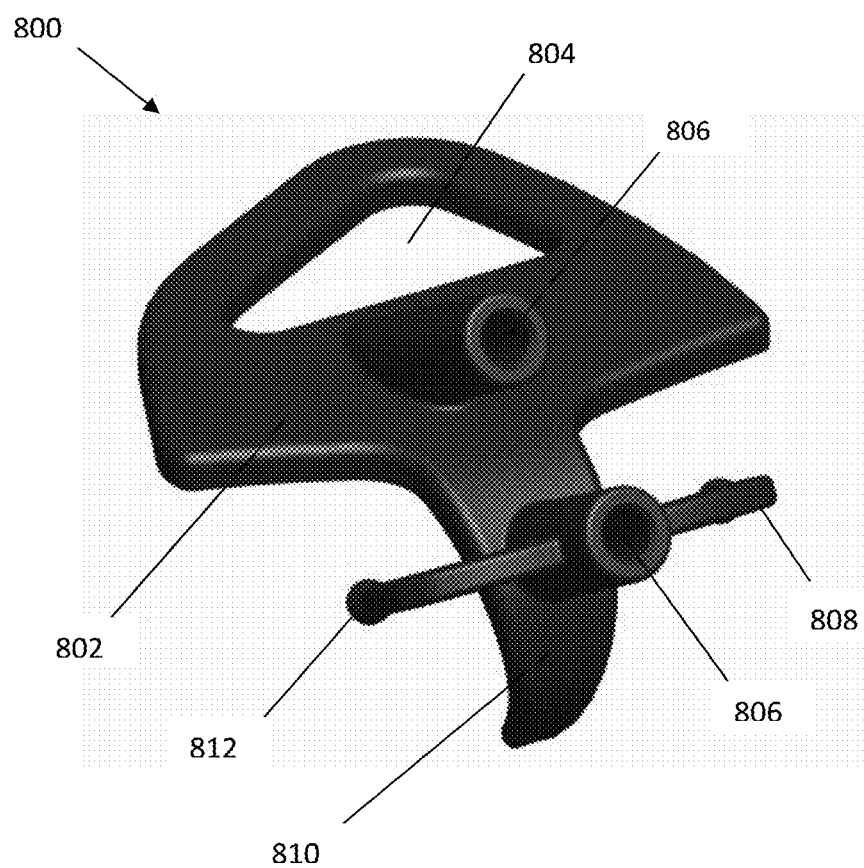
FIG. 11A shows a perspective view of the implant profiler of FIG. 10.
Figure 11B:
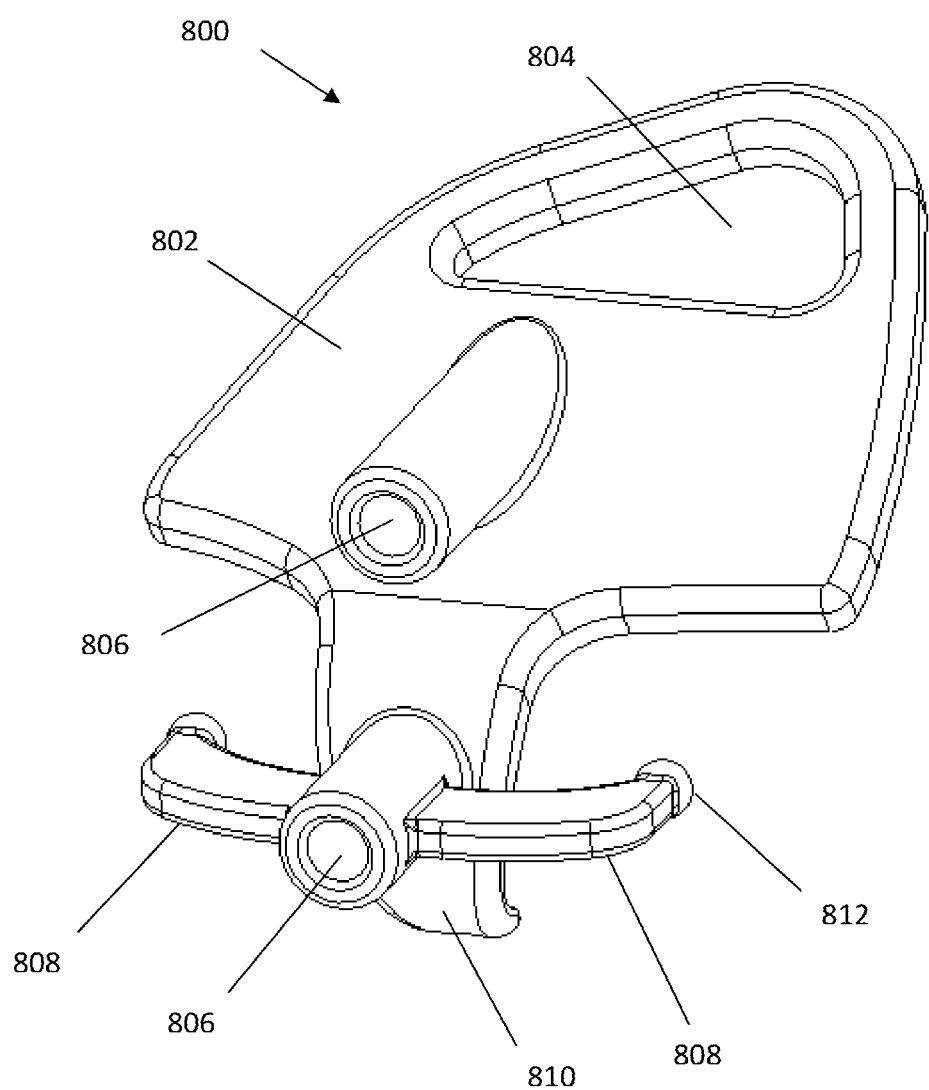
FIG. 11B shows another perspective view of the implant profiler of FIG. 10.

FIG. 9 illustrates an embodiment of the blade runner 700. The blade runner 700 may include a blade 704 and a finger-grip 702. The blade 704 is generally arcuate and flattened and may include an engagement portion 706 at one end. The finger-grip 702 is generally disposed adjacent to the engagement portion 706.

A resection demonstration step may be optionally performed, wherein, with the intercondylar block 200 and resection guide 500 coupled to the femur bone 100, a surgeon grips the finger-grip 702 and inserts the engagement portion 706 into the gap between the resection and restriction plates and pivots the blade runner 700 about the central post 510 of the resection guide 500 until the blade runner 700 extends around the anterior aspect of the femoral condyles. The arcuate shape of the blade 704 provides clearance avoid interference with the femur bone 100. This provides the surgeon with a visual representation of the resection plane in order to verify that the proper height alignment has been achieved. The surgeon may make fine adjustments to the resection height in order to optimize the resection plane location. Once resection has been demonstrated to the approval of the surgeon, resection may be performed with a bone saw through the resection guide 500 to remove a portion of bone from the anterior femoral condyles in preparation to receive a patellofemoral implant.

Figure 12A:
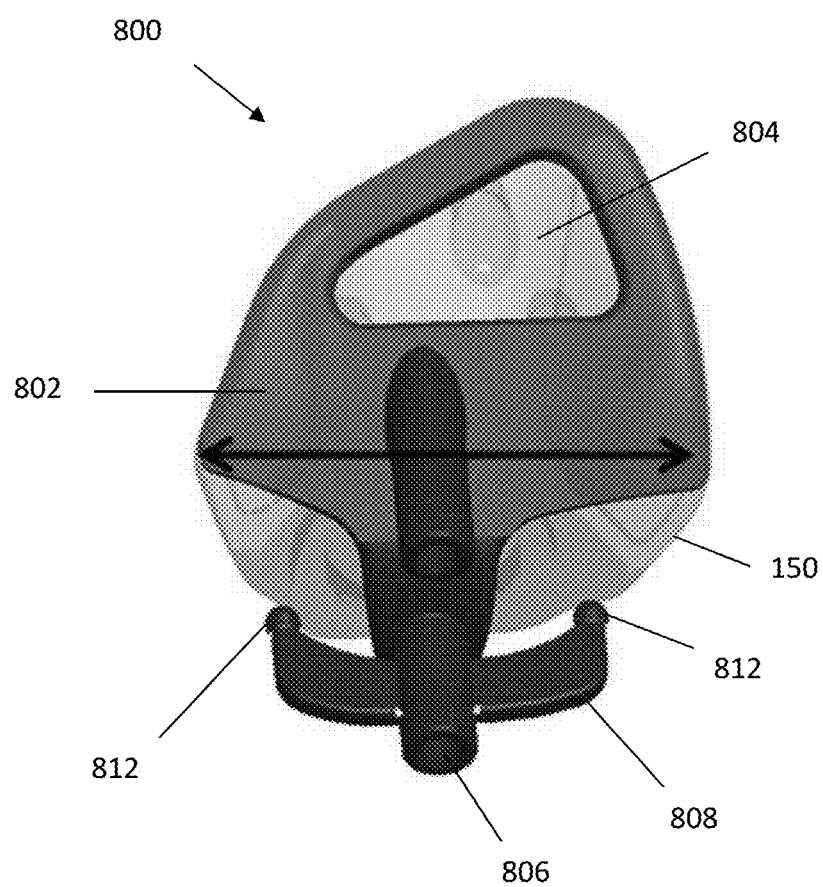
FIG. 12A shows a front view of the implant profiler of FIG. 10 superimposed on a silhouette of a patellofemoral implant.
Figure 12B:
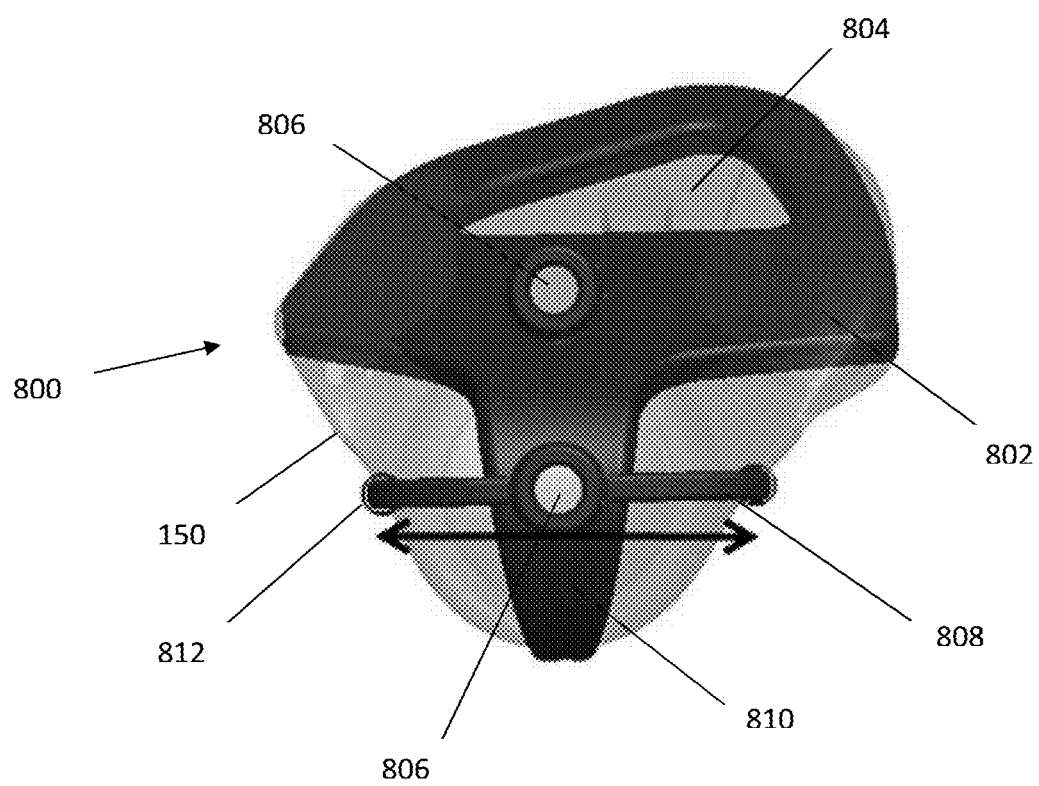
FIG. 12B shows another front view of the implant profiler of FIG. 10 superimposed on a silhouette of a patellofemoral implant.

Once anterior resection is complete, sizing for a patellofemoral implant and preparation for further bone resection may occur. FIGS. 10-12B demonstrate an embodiment of an implant profiler 800. Referring to FIGS. 11A-12B, the implant profiler 800 generally includes a proximal portion 802 and a distal portion 810 extending therefrom. The proximal portion 802 has a bone interface surface that is generally flat in order to substantially match the surface of the anteriorly resected femur bone 100. The proximal portion also includes an alignment window 804 and a bossed pinhole 806 that both extend through the proximal portion 802. The geometry of the periphery of the proximal portion 802 substantially matches that of a portion of a patellofemoral implant as demonstrated by a superimposition of the implant profiler 800 on an implant silhouette 150 of a patellofemoral implant as seen in FIGS. 12A-B. In other words, the periphery of the proximal portion 802 substantially represents the size and shape of a portion of a corresponding patellofemoral implant.

The distal portion 810 extending from the proximal portion 802 is arcuate in order to avoid interference with osteophytes and cartilage when engaged with the femur bone 100. Further, the distal portion 810 is tapered in order to avoid interference with the condyles. The distal portion 802 includes a bossed pinhole 806 that extends through the distal portion 810. A pair of wings 808 may extend from this bossed pinhole 806 in both the lateral and medial directions. Each wing 808 curves into a point that is formed into a contact sphere 812 in order to prevent sharp points from contacting the femur bone 100. The distance each wing 808 extends from the bossed pinhole 806 and the distance the distal portion 810 extends from the proximal portion 802 substantially matches the dimensions of the periphery of a portion of a patellofemoral implant as illustrated by the superimposition of the implant profiler over the implant silhouette 150 of FIGS. 12A-B. Thus, the combination of the proximal portion 802 and distal portion 810 of the implant profiler 800 ensures that the periphery of the implant profiler 800 substantially matches that of a patellofemoral implant in order to appropriately size the patellofemoral implant with respect to the femur bone 100.

In the performance of an embodiment of a sizing and pin placement step, a surgeon places the implant profiler 800 over the resected bone such that the generally flat bone interface surface of the implant profiler 800 planarly engages the anteriorly resected portion of femur bone 100. The window 804 located through the proximal portion 802 provides visual confirmation that the implant profiler 800 is fully seated and flush with the anterior resection. The distal portion 810 is placed within the intercondylar portion of the femur bone 100 with the contact spheres 812 and the end of the distal portion 810 in contact with the femur bone 100. The surgeon, at his or her discretion, determines if the size is appropriate for a corresponding patellofemoral implant. If not, another size may be tried until the appropriate size is determined. Once the appropriate size is chosen, the implant profiler 800 is placed on the femur bone 100. The surgeon then inserts reference pins 106 into the implant profiler 800 through the bossed pinholes 806. These reference pins 106 are used by other surgical instrumentation as a reference and a guide for resecting the femur bone 100 in order to continue to form the femur bone 100 to receive a patellofemoral implant as will be discussed later. Thus, the bossed pinholes 806 of the distal 810 and proximal 802 portions of the implant profiler 800 are precisely located within the implant profiler 800 to correspond with the use of the other surgical instrumentation.

Figure 13:
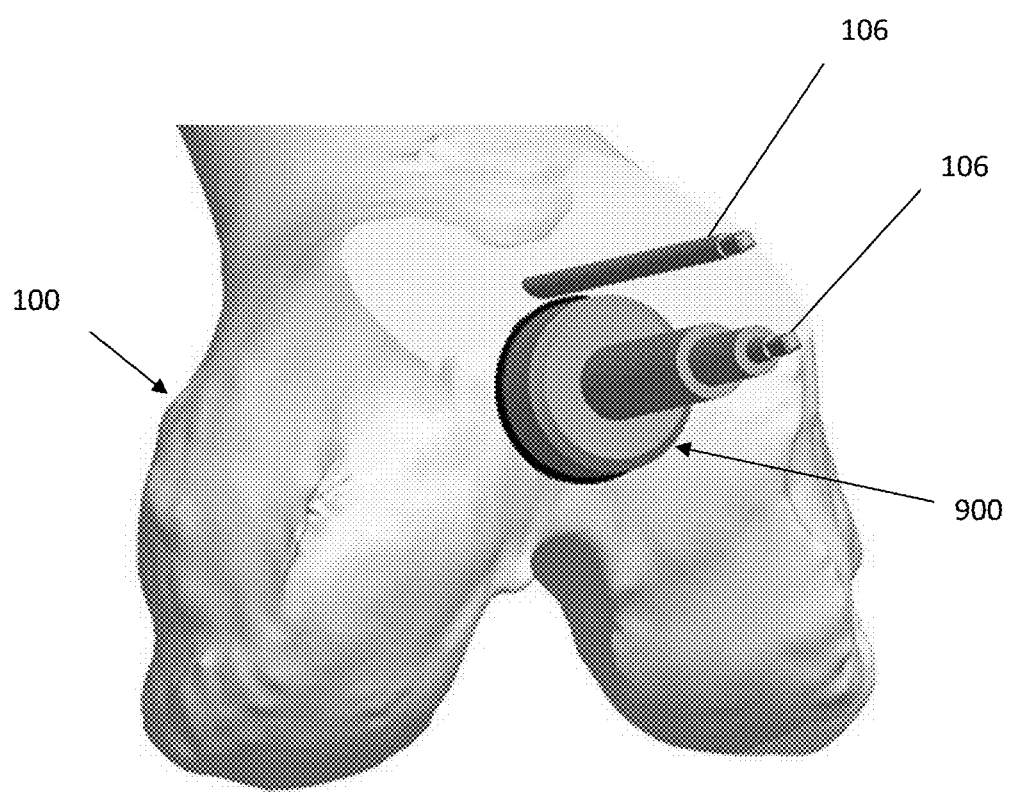
FIG. 13 shows perspective view of a reaming step and a reamer.
Figure 14:
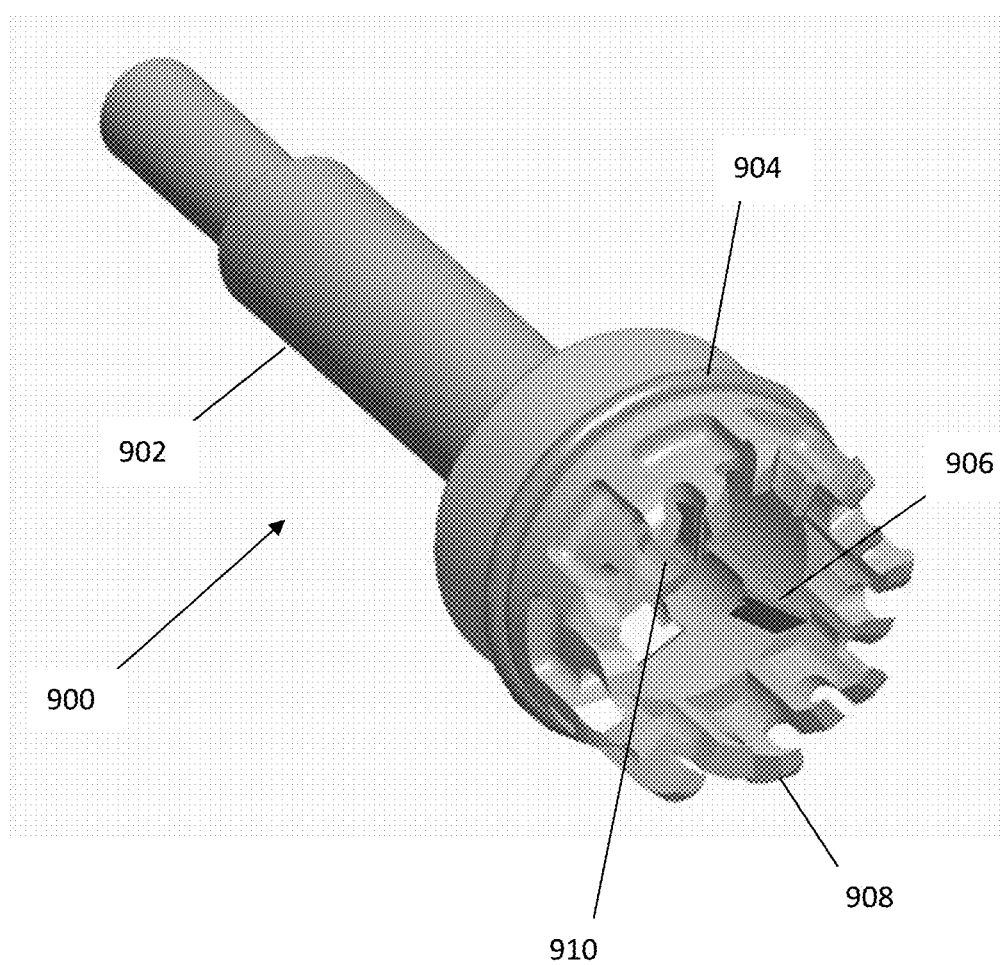
FIG. 14 shows a perspective view of the reamer of FIG. 13.

A reamer 900 as illustrated by FIGS. 13 and 14 is one of the other surgical instruments that references the reference pins 106 located by the implant profiler 800. The reamer 900 generally includes a guide shaft 902, a depth stop 904, and a plurality of cutting blades. The guide shaft 902 may have a cannulated passageway 910 that extends through the center of the guide shaft 902. One end of the guide shaft 902 is adapted to engage a torque applying device, for example a drill chuck. At the other end of the guide shaft 902 resides the plurality of cutting blades.

According to the embodiment illustrated by FIG. 14, the plurality of cutting blades include alternating blades 908 that are disposed along the circumference of the cutting area. The alternating blades 908 alternate in order to provide bone chip clearance so the reamer 900 does not become bogged down with bone fragments. The inner blades 906 reside along the cutting area between the alternating blades 908 and the cannulated passageway 910. The inner blades 906 may be offset from the ends of the alternating blades 908 so that the alternating blades 908 cut deeper into the femur bone 100 than the inner blades 906. The inner blades 906 profile the surface of the femur bone 100 to ensure the surface of femur bone 100 will be flush or with a patellofemoral implant or slightly below/inside the implant to allow for a cement mantle. Adjacent to the alternating blades is a reaming depth stop 904 that is formed by a rim that protrudes radially from the reamer 900. The diameter formed by the reaming depth stop 904 is larger than the diameter formed by the alternating blades 908 in order to prevent the reamer 900 from reaming too deeply.

FIG. 13 shows the end of a reaming step. With the reference pins 106 in place, the cannulated passageway 910 may be placed over the reference pin 106 that had been guided by the bossed pinhole 806 of the distal portion 810 of the implant profiler 800. A torque is delivered to the reamer 900, thereby resecting the femur bone 100 until the reaming depth stop 904 prevents further resection. This may form a void in the femur bone 100 to receive a circular rim of a circular rim implant (discussed later), or contour the bone surface for more precise engagement with a bone interface surface of a patellofemoral implant.

Figure 15:
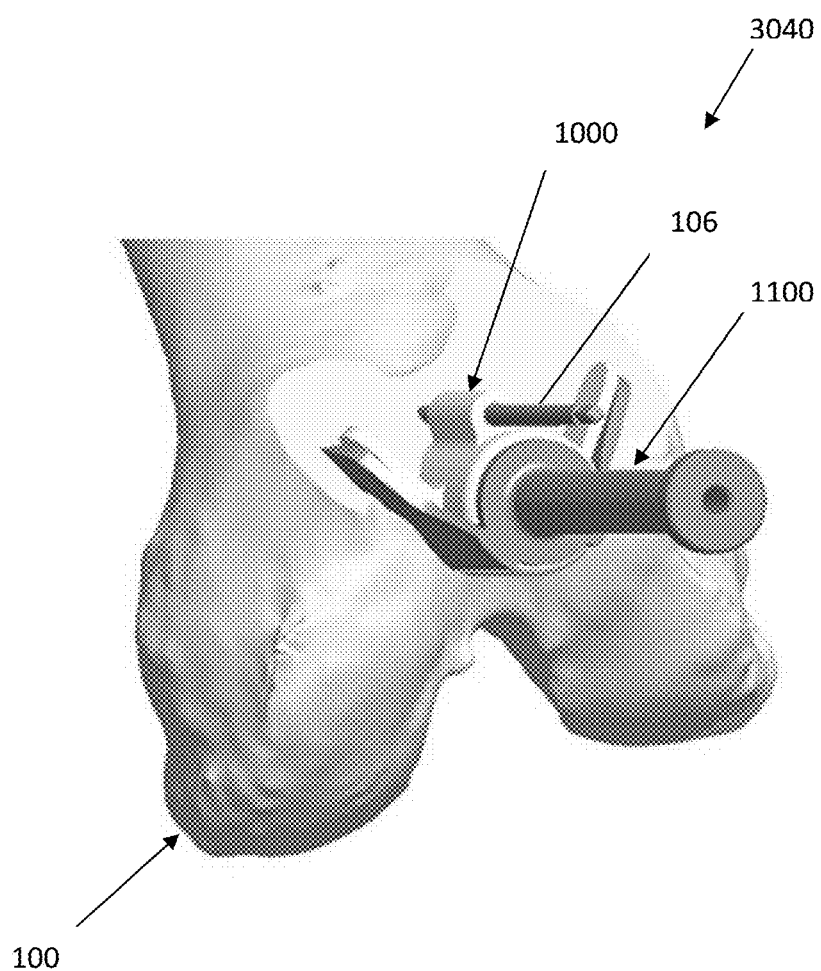
FIG. 15 shows a perspective view of a trochlear punch assembly having a punch guide and a multiblade punch.

Another surgical instrument that references the reference pins 106 located by the implant profiler 800 is a trochlear punch assembly 3040. FIG. 15 illustrates an embodiment of the trochlear punch assembly 3040 in accordance with the present invention. The trochlear punch assembly 3040 generally includes a punch guide 1000 and a multiblade punch 1100.

Figure 16:
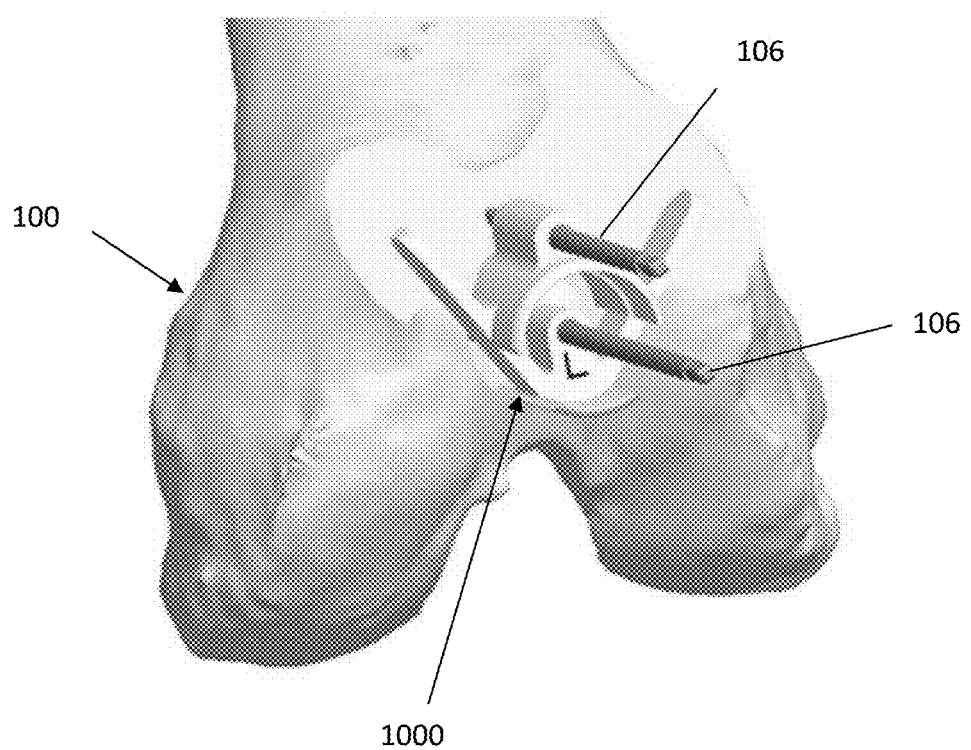
FIG. 16 shows a perspective view of the punch guide of FIG. 15 situated with respect to a femur bone.
Figure 17:
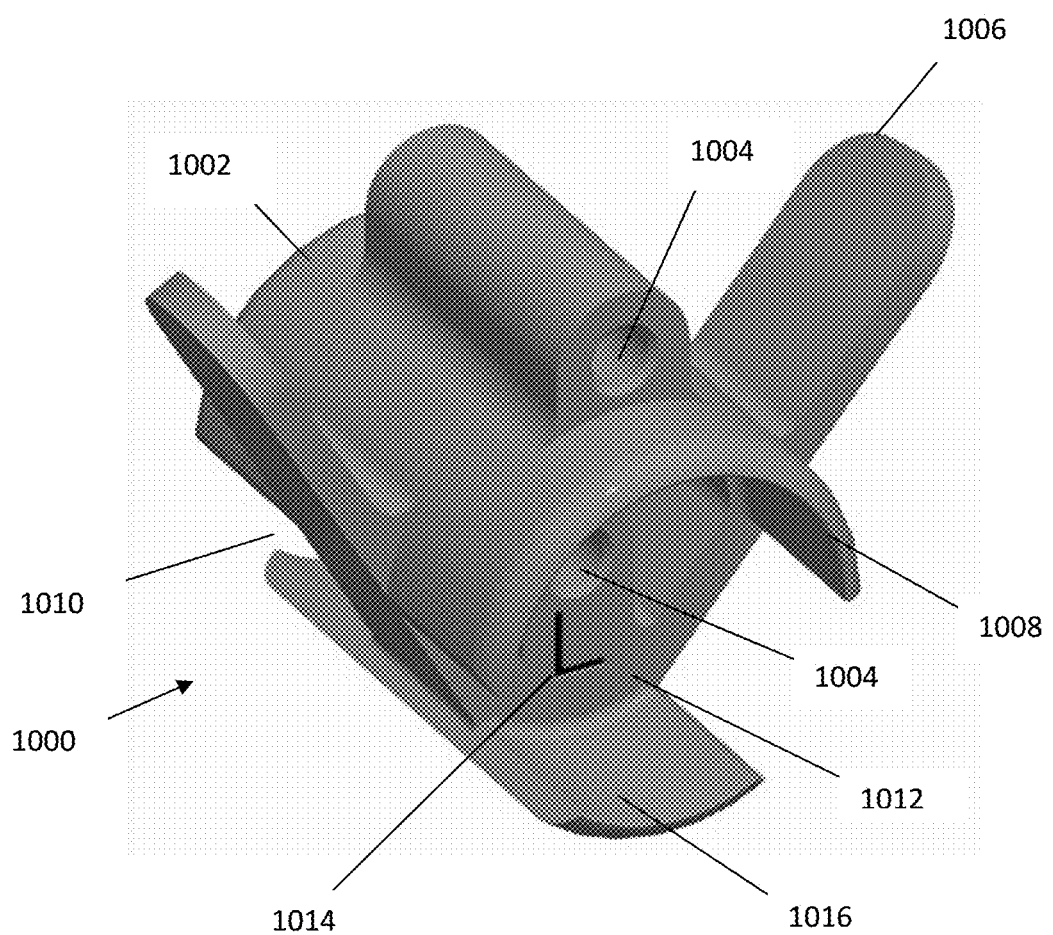
FIG. 17 shows a perspective view of the punch guide of FIG. 15.

FIGS. 16 and 17 show an embodiment of the punch guide 1000. The punch guide 1000 is universal such that one punch guide 1000 may be used for both knees. The punch guide 1000 generally includes a cylindrical body 1002, alignment pinholes 1004, and a pair of blade guides 1006. The cylindrical body 1002 may have a central passageway that extends therethrough. A wall may reside within the central passageway providing a depth stop surface 1012 located on each side of the wall. Indicator markings 1014 may be disposed on each depth stop surface 1012 to indicate to the surgeon the proper orientation of the punch guide 1000 depending on the leg for which the patellofemoral replacement procedure is being performed. The distance from each of the depth stop surfaces 1012 to the end of the cylindrical body 1002 forms a rim 1016, which facilitates the translational guidance of the multiblade punch 1100. An alignment pinhole 1004 extends through the depth stop surfaces 1012 generally through the center of the punch guide 1000. Another alignment pinhole 1004 is disposed along the external surface of the cylindrical body 1002 in parallel alignment with the alignment pinhole 1004 located within the cylindrical body 1002. Grooves 1010 run the length of the cylindrical body 1010 and extend into the central passageway. The blade guides 1006 extend from the internal passageway through these grooves 1010. The blade guides 1006 are angled with respect to each other to form a "V" configuration.

Figure 18:
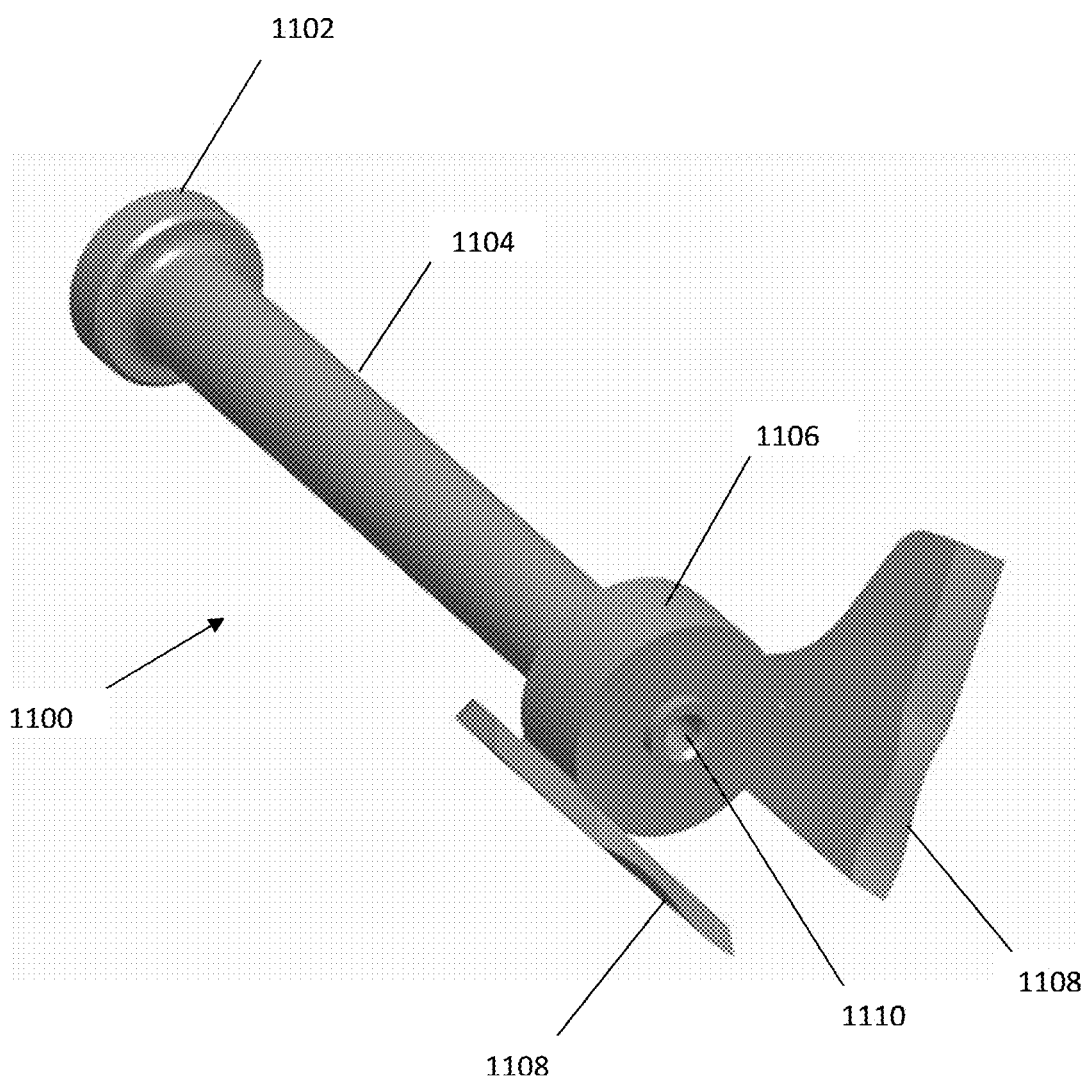
FIG. 18 shows a perspective view of the multiblade punch of FIG. 15.

FIG. 18 shows the multiblade punch 1100 according to an embodiment of the present invention. The multiblade punch 1100 generally includes a handle 1104 with an impact region 1102 disposed on one end of the handle 1104 and an annular region 1106 disposed on the other end of the handle 1104. A cannulated passageway 1110 extends through the annular region 1106 into the handle 1104. A pair of punch blades 1108 are tangentially disposed on the outer surface of the annular region 1106. The punch blades 1108 are angled with respect to each other to form a "V" configuration that substantially matches the "V" configuration of the blade guides 1106 and to substantially match the periphery of a trochlear region of a patellofemoral implant. The multiblade punch 1100 may be monolithic. In another embodiment, the handle 1104 may be modular such that it can accept blades that correspond to different sized patellofemoral implants.

FIGS. 15 and 16 show a bone punching step. Referring to FIG. 16, the punch guide 1000 is placed over the reference pins 106 that were located by the implant profiler 800. The alignment pinhole 1004 that extends through the center of the cylindrical body 1002 is slid over the most distal reference pin 106, and the alignment pinhole 1004 that is disposed on the outer surface of the cylindrical body 1002 is slid over the most posterior reference pin 106. The alignment pinholes 1004 and reference pins 106 place the punch guide 1000 in the proper position on the femur bone 100 as well as at setting the proper rotational alignment. Where the procedure is being performed on the left leg, the surgeon will orient the punch guide 1000 such that the indicator marking 1014 indicating the left leg is facing the surgeon. Where the procedure is being performed on the right knee, the indicator marking 1014 indicating the right knee is set facing the surgeon. As the punch guide 1000 is slid over the reference pins 106, the cylindrical body 1002 is inserted into the bone void formed by the reamer 900. Thus, the diameter of the cylindrical body 1002 is dictated by the diameter of the reamer 900, which is in turn dictated by the size of the corresponding patellofemoral implant.

With the punch guide 1000 set in place, the multiblade punch 1100 is guided by the punch guide 1000. The cannulated passageway 1110 of the multiblade punch 1100 is slid over the most distal reference pin 106. As this occurs, the annular region 1106 is guided by the rim 1016 formed by the cylindrical body 1002. Additionally, rotational orientation of the multiblade punch 1100 is guided by the grooves 1010 in the cylindrical body 1002 and the blade guides 1006. An impulse force is applied to the impact region 1102 of the handle 1104 until the annular region 1106 abuts the depth stop surface 1012, at which point the appropriate punch depth has been achieved. Once the proper depth is achieved, the multiblade punch and punch guide is removed from the femur bone 100 in preparation for further bone resection.

Figure 19:
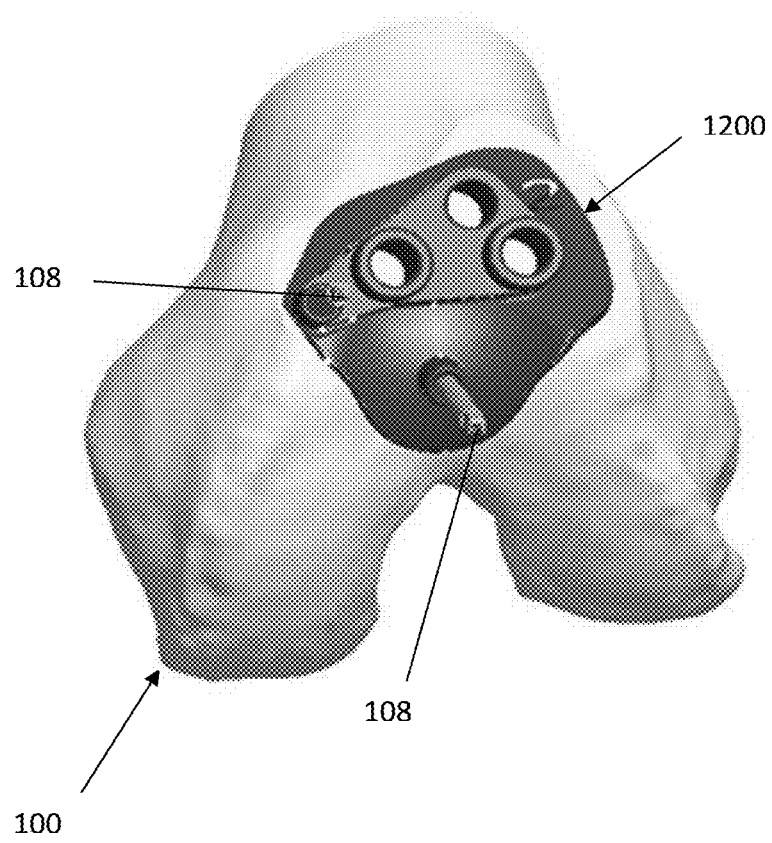
FIG. 19 shows a perspective view of a circular rim drill template.
Figure 20:
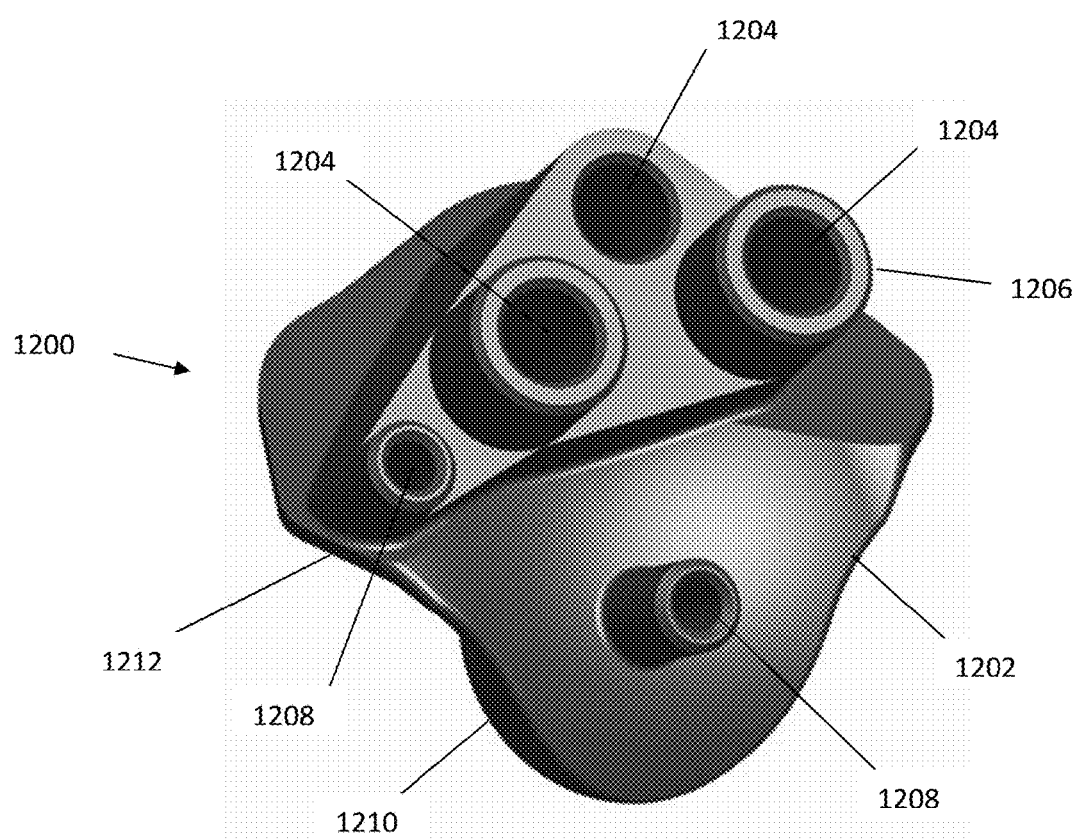
FIG. 20 shows a perspective view of the circular rim drill template of FIG. 19.

FIGS. 19 and 20 show a circular rim drill template 1200 according to an embodiment of the present invention. The circular rim drill template 1200 has a bone interface surface and a plurality of holes extending therethrough. The plurality of holes include retainment pinholes 1208 and drill guide holes 1204. The drill guide holes 1204 may be bossed and may have a drill stop shoulder 1206 to act as a drill depth stop. The length of the boss is determined by the desired depth of cut. Thus, some drill guide holes 1204 may not be bossed if greater depth is desired. The locations and number of the drill guide holes 1204 within the circular rim drill template 1200 directly correspond to the locations and number of bone pegs disposed on a corresponding circular rim implant (discussed later). Generally there are at least two retainment pinholes 1208 that have longitudinal axes that may be angled with respect to one another in order to prevent lift-off and rotation when coupled to the femur bone 100. The bone interface surface has a distal portion that may include a circular rim 1210. The bone interface surface may also have peripheral flanges 1212 extending from the bone interface surface along the boundary of the circular rim drill template 1200 for engaging the section of bone resected by the multiblade punch 1100. The circular rim 1210 has a diameter that substantially corresponds to the bone void created by the reamer 900. The periphery of the circular rim drill template 1200 substantially matches the periphery of a corresponding circular rim implant. In other words, the profile of the circular rim drill template 1200 is substantially similar to that of a corresponding circular rim implant such that the surgeon has an accurate visual representation of the size, shape and fit of the circular rim implant when he or she drills via the circular rim drill template 1200. Thus, the circular rim drill template 1200 provides the surgeon with an accurate depiction of the circular rim implant so that he or she can properly locate the drill guide holes 1204 with respect to the femur bone.

FIG. 19 shows the initiation of a drilling step. The circular rim drill template 1200 is positioned onto the femur bone 100 such that the circular rim 1210 is disposed within the bone void created by the reamer 900. A proximal portion of the bone interface surface planarly engages the anterior resected portion of the femur bone 100. Rotation of the circular rim drill template 1200 is set by the engagement of the peripheral flanges 1212 with the multiblade punched portion of bone. Once the circular rim drill template 1200 is properly seated, the surgeon inserts retainment pins 108 into the retainment pinholes 1208 to prohibit movement of the circular rim drill template 1200 during drilling. The surgeon then drills a series of holes into the femur bone 100 through the drill guide holes 1204 to a depth dictated by the length of the boss of the drill guide holes 1204. The retainment pins 108 and circular rim drill template 1200 is removed so that the corresponding circular rim implant may be implanted on the femur bone 100.

Although the invention thus far has been described with reference to particular embodiments, it is to be understood that these embodiments are merely illustrative of the principles and applications of the present invention. The implant profiler 800, reamer 900, trochlear punch assembly 3040, and circular rim drill template 1200 are merely one embodiment for preparing a femur bone 100 to receive a patellofemoral implant, more particularly a circular rim implant, for example. However, other instrumentation and methods may be utilized to prepare bone for the circular rim implant and other embodiments of patellofemoral implants that would fall align with the principles disclosed herein.

Figure 21:
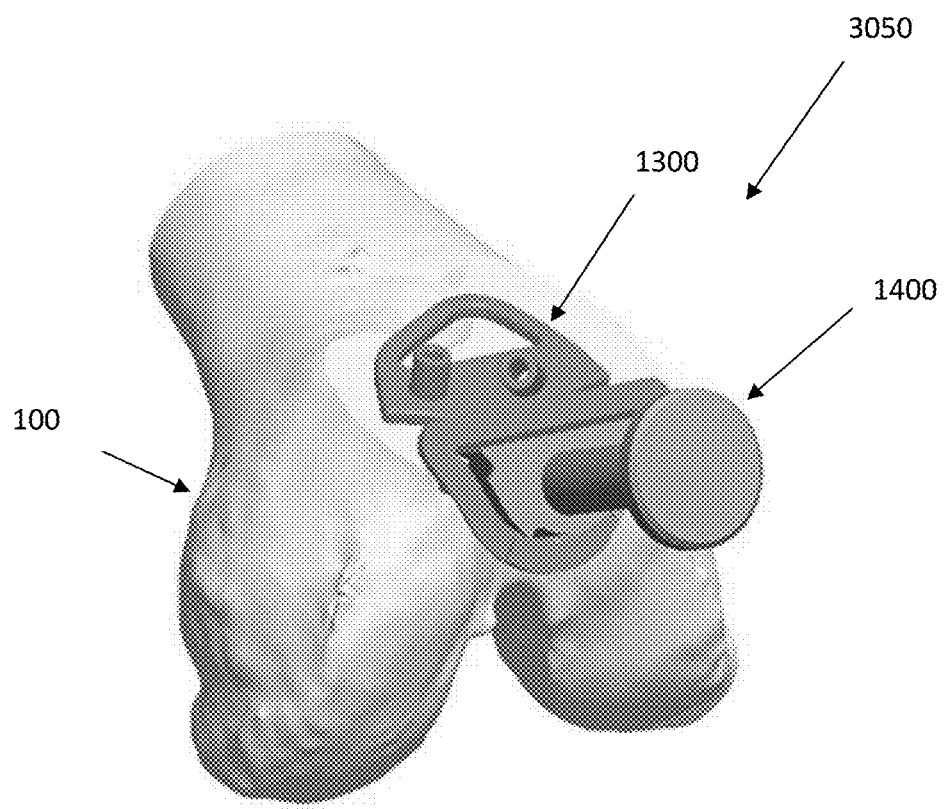
FIG. 21 shows a perspective view of a sizing and pinning step, a punching step and a multifunction assembly having a two-in-one device and a uniblade punch.

Another exemplary embodiment for preparing bone once anterior resection of the femur bone 100 has taken place is a multifunction assembly 3050 as shown in FIG. 21. The multifunction assembly 3050 is described herein as corresponding with the preparation of a femur bone 100 to receive a rimless implant, for example. However, this discussion is merely an example.

Figure 22:
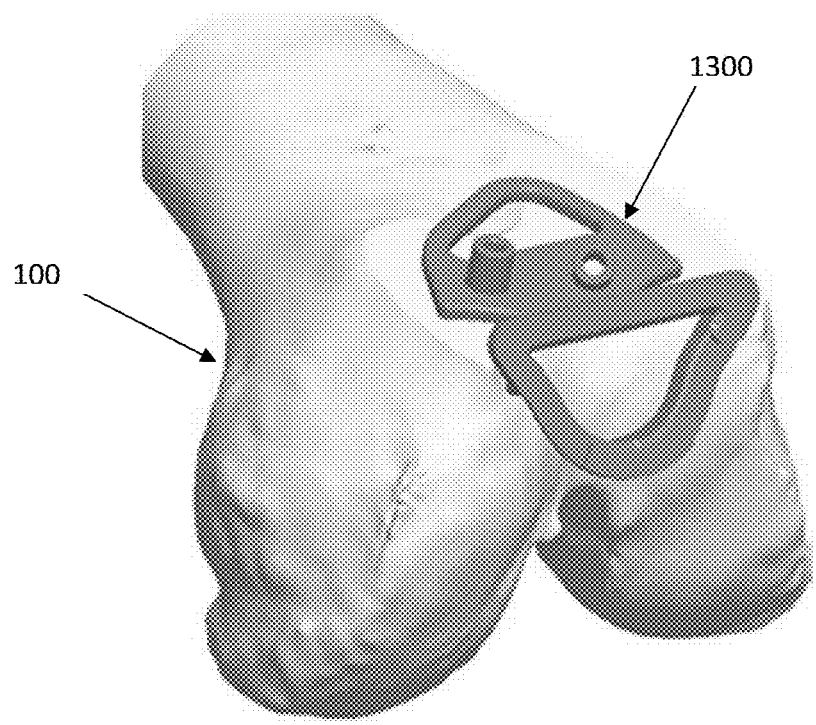
FIG. 22 shows a perspective view of the two-in-one device of FIG. 21 with respect to a femur bone.
Figure 23:
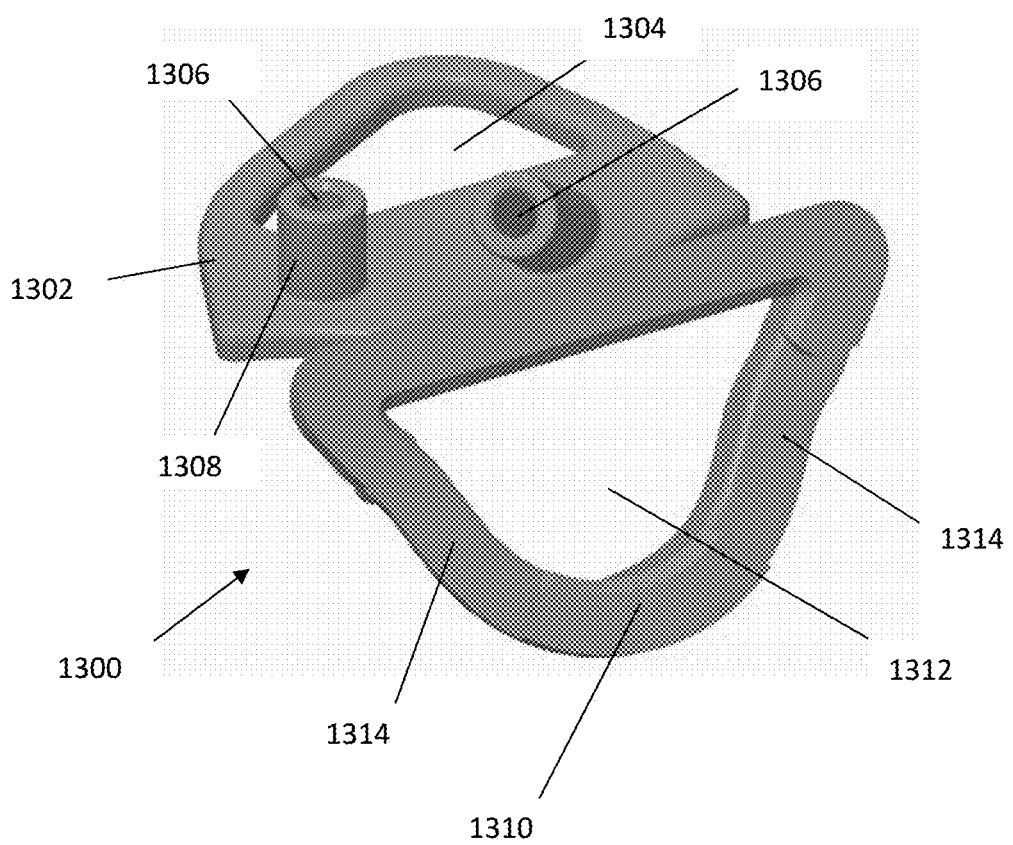
FIG. 23 shows a perspective view of the two-in-one device of FIG. 21.

The multifunction assembly 3050 generally includes a two-in-one device 1300 and a uniblade punch 1400. FIGS. 22 and 23 illustrate the two-in-one device 1300, which generally includes a proximal portion 1302 and a distal portion 1310 extending therefrom. The proximal portion 1302 has a bone interface surface that is generally flat in order to substantially match the surface of the anteriorly resected femur bone 100. The proximal portion 1202 also includes an alignment window 1304 and at least two retainment pinholes 1206 extending through the proximal portion. At least one of the retainment pinholes 1306 is obliquely angled with respect to the bone interface surface of the two-in-one device 1300 to prohibit lift-off of the two-in-one device 1300 from the femur bone 100. The geometry of the periphery of the proximal portion substantially matches that of a portion of a patellofemoral implant. In other words, the proximal portion 1202 of the two-in-one device 1300 substantially represents the size and geometry of a portion of a patellofemoral implant.

The distal portion 1310 extending from the proximal portion 1302 has a planar surface that is angled with respect to the bone interface surface of the proximal portion 1302 such that the distal portion 1310 extends along the trochlear region of the femur bone 100 when the proximal portion 1302 is engaged with the anterior resection of the femur bone 100. The distal portion 1310 has a punch guide window 1312 that extends therethrough and is dimensioned to receive the uniblade punch 1400. The punch guide window 1312 forms a rim along the perimeter of the punch guide window 1312. The rim is flanged and chamfered to allow for easy insertion of the uniblade punch 1400 and to guide the uniblade punch 1400 by accurately matching its shape. Along the rim is a plurality of cutouts 1314 that form depressions in the rim. The distal portion 1310 also has a bone contact surface. Material is removed from the bone contact surface to allow for clearance of ostephytes and cartilage. Three spherical points are disposed on the bone contact surface to reference the most distal, medial and lateral points of which a corresponding implant would extend while in the same position.

Thus, the combined dimensions of the proximal portion 1302 and spherical points of the distal portion 1210 of the two-in-one device 1300 provides an accurate representation of the periphery of a corresponding patellofemoral implant in order to appropriately size the corresponding patellofemoral implant.

FIG. 22 illustrates the initiation of a sizing step for the sizing of a patellofemoral implant. The surgeon places the two-in-one device 1300 over the femur bone 100 such that the generally flat bone interface surface of the proximal portion 1302 of the two-in-one device 1300 planarly engages the anteriorly resected portion of femur bone 100. The alignment window 1304 located in the proximal portion 1302 provides visual confirmation that the two-in-one device 1300 is fully seated and flush with the anterior resection. The distal portion 1310 is positioned over the trochlear region of the femur bone 100, and the spherical points of the distal portion 1310 are placed into contact with the femur bone 100. The surgeon, at his or her discretion, determines if the size is appropriate for a corresponding patellofemoral implant. If not, another size may be tried until the appropriate size is determined. Once the appropriate size is chosen and properly placed on the femur bone 100, the surgeon will insert retainment pins into the two-in-one device 1400 through the retainment pinholes 1306. These retainment pins secure the two-in-one device from rotation and lift-off.

Figure 24:
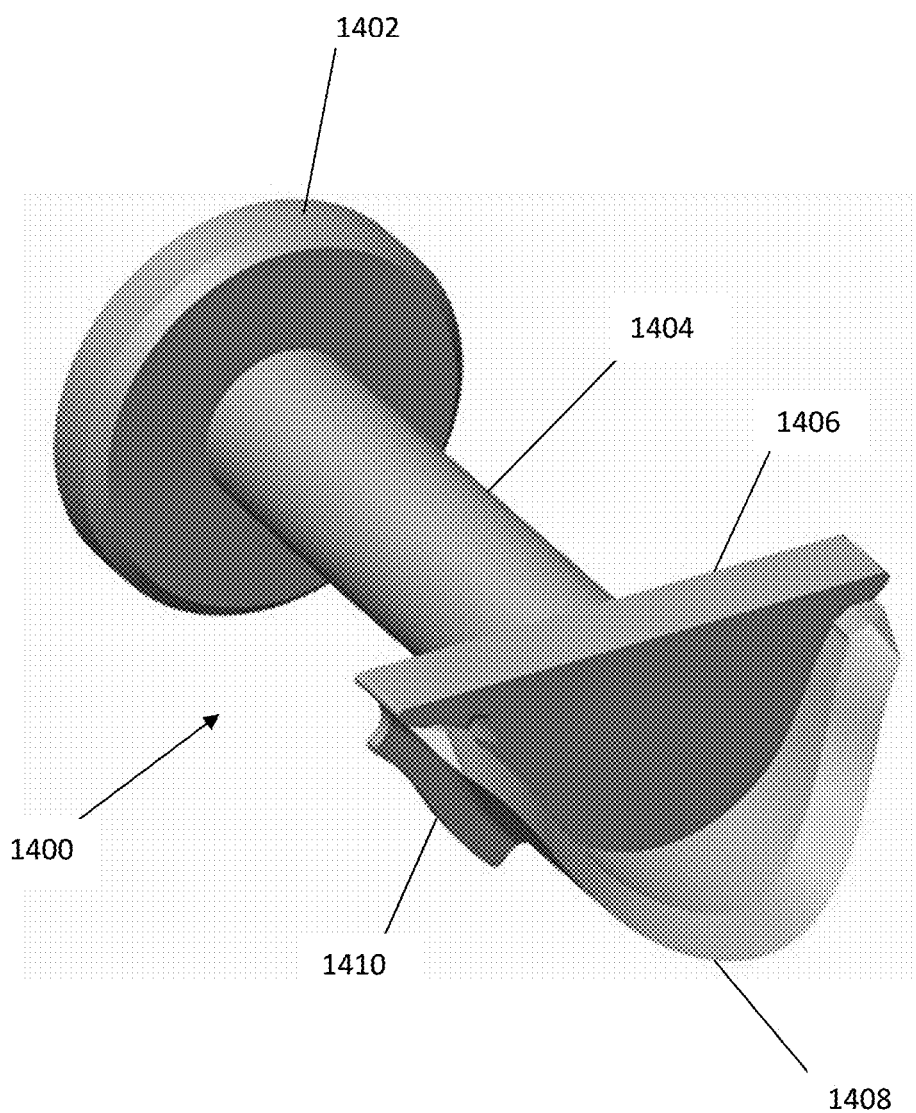
FIG. 24 shows a perspective view of the uniblade punch of FIG. 21.

FIG. 24 shows the uniblade punch 1400 of the trochlear punch assembly 3050. The uniblade punch 1400 generally has a handle 1404 with an impact region 1402 disposed at one end of the handle 1404 and a transverse wall 1406 disposed at the other end. The uniblade 1408 extends from the transverse wall 1406 parallel to the longitudinal axis of the handle 1404. The uniblade 1408 is generally curvilinear to substantially match the contours of a corresponding patellofemoral implant and the punch guide window 1312 of the two-in-one device 1300. The transverse wall 1406 also has a plurality of tabs 1410 that extend from the transverse wall 1410 in a direction generally perpendicular to the longitudinal axis of the handle 1404. The plurality of tabs 1410 are configured and positioned on the transverse wall 1406 such that they interface with the cutouts 1314 of the distal portion 1310 of the two-in-one device 1300 during punching. The handle 1404 may be modular in order to interface with various punch sizes. However, the uniblade punch 1400 may be entirely monolithic.

FIG. 21 shows a trochlear punch step. With the two-in-one device 1300 attached to the femur bone 100, the uniblade punch 1408 is inserted into the punch guide window 1312 of the two-in-one device 1300. An impulse force is applied to the impact region 1402. As the uniblade 1408 penetrates the femur bone 100, the plurality of tabs 1410 engage the cutouts 1314 to provide added guidance and to act as a depth stop to prevent the uniblade 1408 from penetrating too deeply. Once the proper depth is achieved, the uniblade punch 1400 and two-in-one device 1300 is removed from the femur bone 100 in preparation for further bone resection.

Figure 25:
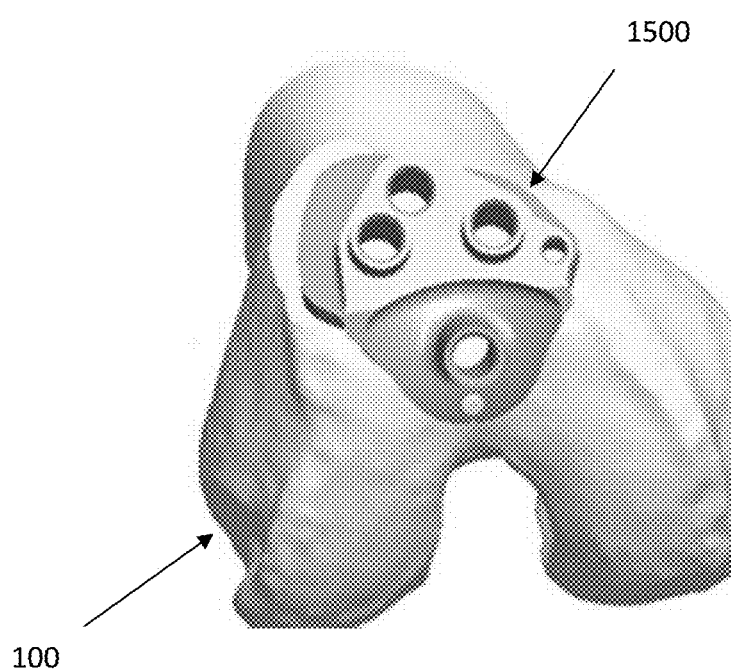
FIG. 25 shows a perspective view of another embodiment of a drilling step and a rimless drill template situated with respect to a femur bone.
Figure 26:
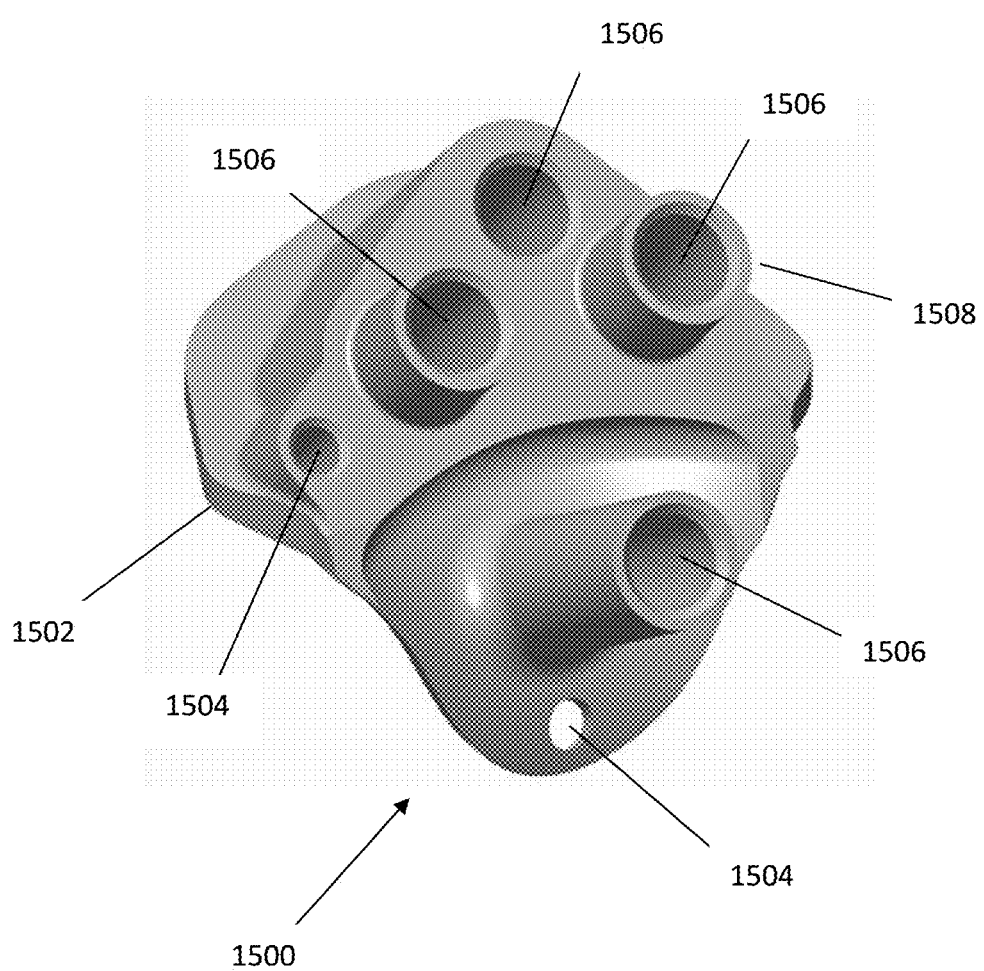
FIG. 26 shows a perspective view of the rimless drill template of FIG. 25.

FIGS. 25 and 26 show a rimless drill template 1500 according to an embodiment of the present invention. The rimless drill template 1500 has a bone interface surface and a plurality of holes extending therethrough. The plurality of holes include retainment pinholes 1504 and drill guide holes 1506. The drill guide holes 1506 may be bossed and may have a drill stop shoulder 1508 to act as a drill depth stop. The length of the boss is determined by the desired depth of cut. Thus, some drill guide holes 1506 may not be bossed if greater depth is desired. The locations and number of the drill guide holes 1506 within the rimless drill template 1500 directly correspond to the locations and number of bone pegs disposed on a corresponding rimless implant (discussed later). Generally there are at least two retainment pinholes 1504 that have longitudinal axes that may be angled with respect to one another in order to prevent lift-off and rotation when coupled to the femur bone 100. The bone interface surface may have peripheral flanges extending from the bone interface surface for engaging the section of bone resected by the uniblade punch 1400. The periphery of the rimless drill template 1500 substantially matches the periphery of a corresponding rimless implant. In other words, the profile of the rimless drill template 1500 is substantially similar to that of a corresponding rimless implant such that the surgeon has an accurate visual representation of the size, shape and fit of the rimless implant when he or she drills via the circular rim drill template 1500. Thus, the rimless drill template 1500 provides the surgeon with an accurate depiction of the rimless implant so that he or she can properly locate the drill guide holes 1506 with respect to the femur bone 100.

FIG. 19 shows the initiation of a drilling step. The rimless drill template 1500 is positioned onto the femur bone 100 such that the peripheral flanges are disposed within the bone void created by the uniblade punch 1400. A proximal portion of the bone interface surface planarly engages the anterior resected portion of the femur bone 100. Rotation of the rimless drill template 1500 is set by the engagement of the peripheral flages with the uniblade punched portion of bone. Once the circular rimless drill template 1500 is properly seated, the surgeon inserts retainment pins into the retainment pinholes 1504 to prohibit movement of the rimless drill template 1500 during drilling. The surgeon then drills a series of holes into the femur bone 100 through the drill guide holes 1506 to a depth dictated by the drill guide holes 1506. The retainment pins and rimless drill template 1500 is removed so that the corresponding rimless implant may be implanted on the femur bone 100.

FIGS. 27-30 show yet other embodiments for preparing a femur bone 100 to receive a patellofemoral prosthesis. FIGS. 27-29D illustrate a trochlear trajectory assembly ("TT assembly") 3060. The TT assembly 3060 generally includes a monolithic trochlear trajectory finder ("monolithic TTF") 1600, a spiked sleeve 110, and alignment handles 400.

Referring to FIGS. 28A-29D, the monolithic TTF 1600 generally includes wings 1620, an alignment platform 1624, a first alignment hole 1602, a second alignment hole 1614, a first reference pinhole 1606, a second reference pinhole 1610, a posterior projection 1626 and a stylus 1616. The body is generally narrow compared to its thickness and may have an anterior surface 1612, an inferior surface 1604, a superior surface 1628, a posterior surface 1630, a chamfer surface 1608 and L-M surfaces 1622. The anterior surface 1600 and inferior surface 1604 are generally orthogonal with respect to each other and separated by a chamfer surface 1608. The first alignment hole 1602 extends from the inferior surface 1604 into the monolithic TTF 1600. An alignment platform 1624, similar to that of the intercondylar block 200, is disposed adjacent to the first alignment hole 1602 extending from the inferior surface 1604. The first reference pinhole 1606 extends into the chamfer surface 1608, while the second pinhole 1610 and second alignment hole 1614 extend into the anterior surface 1612. The alignment holes 1602, 1614 preferably do not extend all the way through the monolithic TTF 1600, while the first and second reference pinholes 1606, 1610 extend entirely through the monolithic TTF 1600. The longitudinal axis of the first alignment hole 1602 is generally perpendicular to the anterior surface 1612, the longitudinal axis of the first reference pinhole 1606 is perpendicular to the chamfer surface 1608, and the longitudinal axis of the second alignment hole 1614 is perpendicular to the inferior surface 1604. The longitudinal axis of the second reference pinhole 1610 is oblique with respect to the proximal surface 1612 and parallel to the longitudinal axis of the first reference pinhole 1606. The first reference pinhole 1602 has a larger diameter than the second pinhole 1610 in order to receive the spiked sleeve 110. The first and second pinholes 1606, 1610 are precisely located within the monolithic TTF 1600 such that reference pins 106 inserted through the first and second reference pinholes 1606, 1610 may be used to align and guide other bone preparation instrumentation, for example reamer 900 and captured resection guide 1700 (discussed below).

Figure 28A:
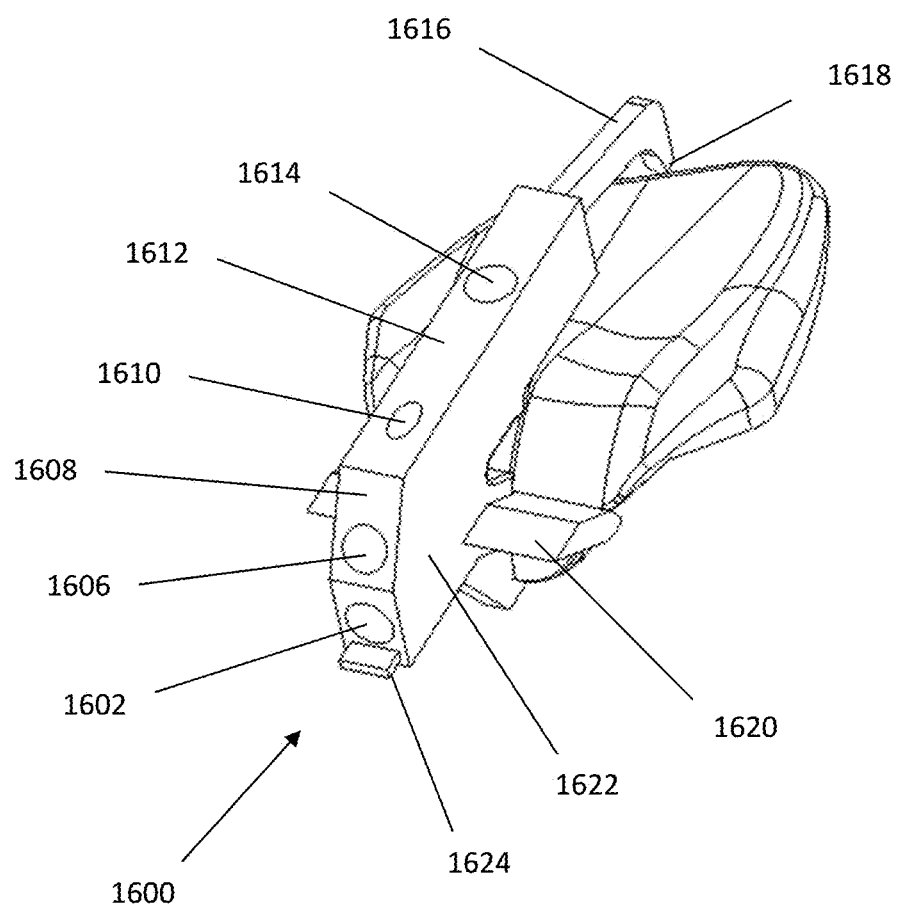
FIG. 28A shows a perspective view of the monolithic TTF of FIG. 27 superimposed on a patellofemoral implant.
Figure 28B:
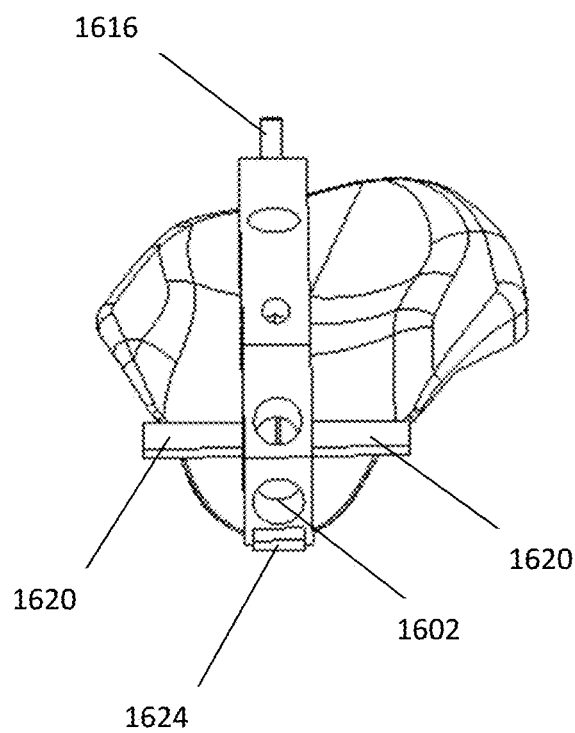
FIG. 28B shows a front view of the monolithic TTF of FIG. 27 superimposed on a patellofemoral implant.
Figure 29A:
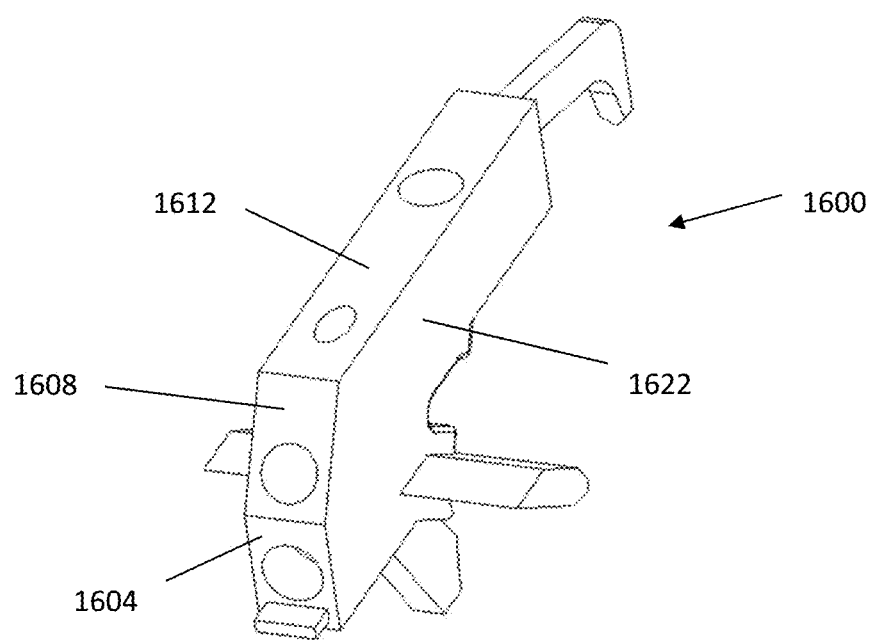
FIG. 29A shows a perspective view of the monolithic TTF of FIG. 27.
Figure 29B:
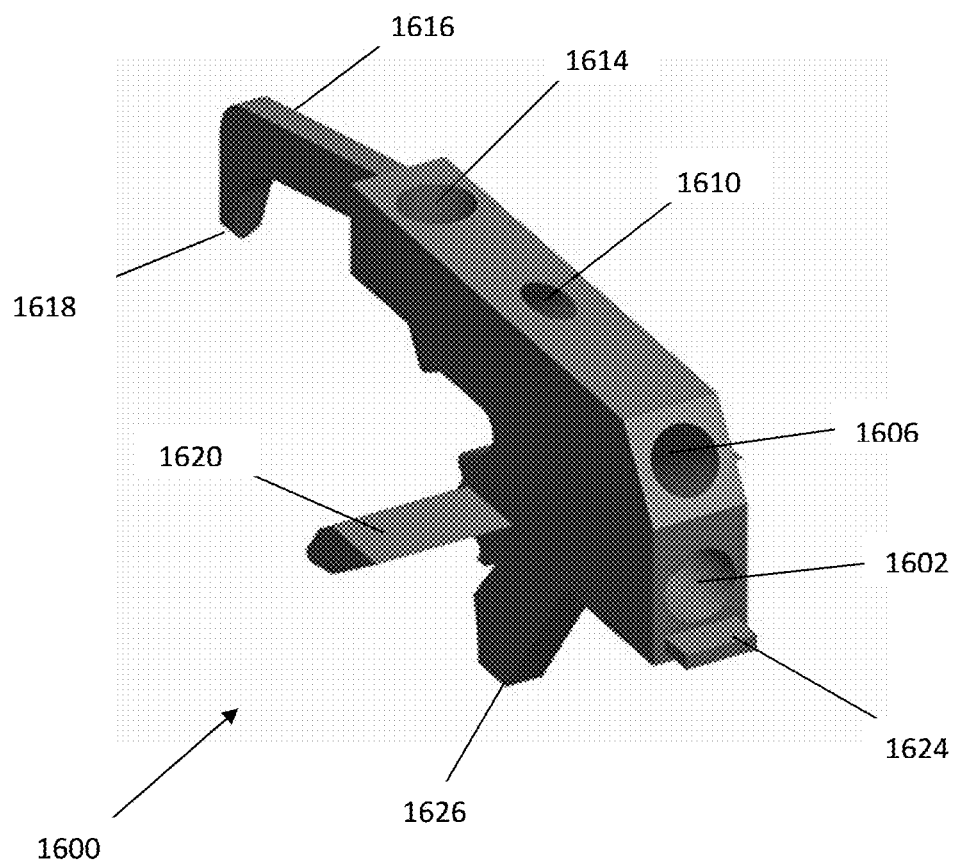
FIG. 29B shows another perspective view of the monolithic TTF of FIG. 27.
Figure 29C:
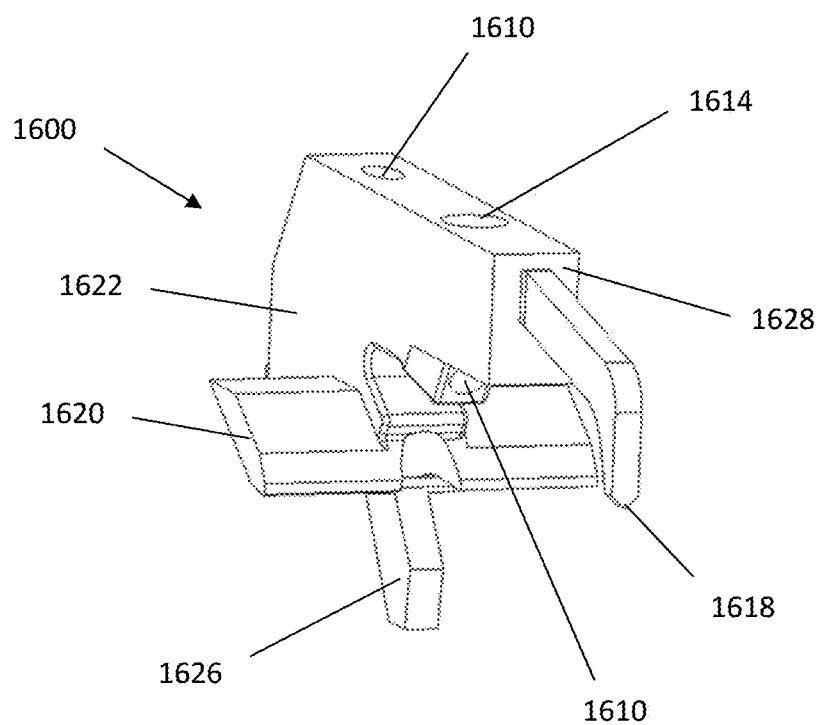
FIG. 29C shows a rear perspective view of the monolithic TTF of FIG. 27.
Figure 29D:
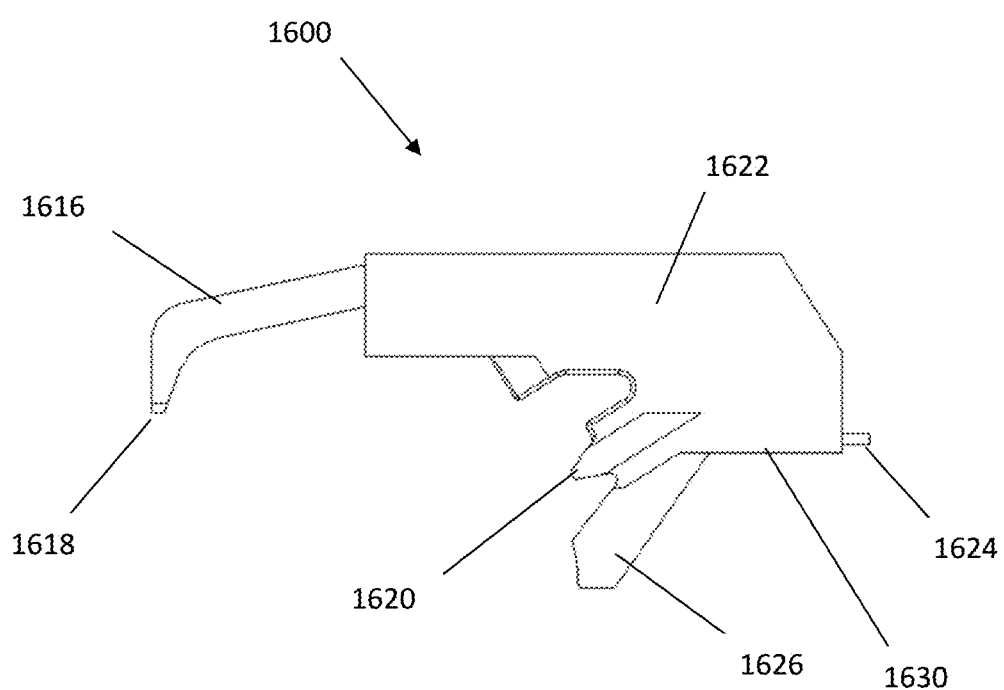
FIG. 29D shows a side view of the monolithic TTF of FIG. 27.

A stylus extends 1616 from the superior surface 1628 and terminates at a stylus tip 1618. At the other end of the monolithic TTF 1600, the posterior projection extends 1626 from the posterior surface 1630. The wings 1620 extend from the L-M surfaces 1622. Referring to FIGS. 28A and 28B, the monolithic TTF 1600 is shown superimposed over a patellofemoral implant. The stylus tip 1618, the wings 1620, and the posterior projection 1626 represent the periphery of a patellofemoral implant as shown in FIGS. 28A and 28B. Thus, the stylus tip 1618, posterior projection 1626, and wings 1620 provide the surgeon with an accurate representation as to the size and profile of a corresponding patellofemoral implant.

Figure 27:
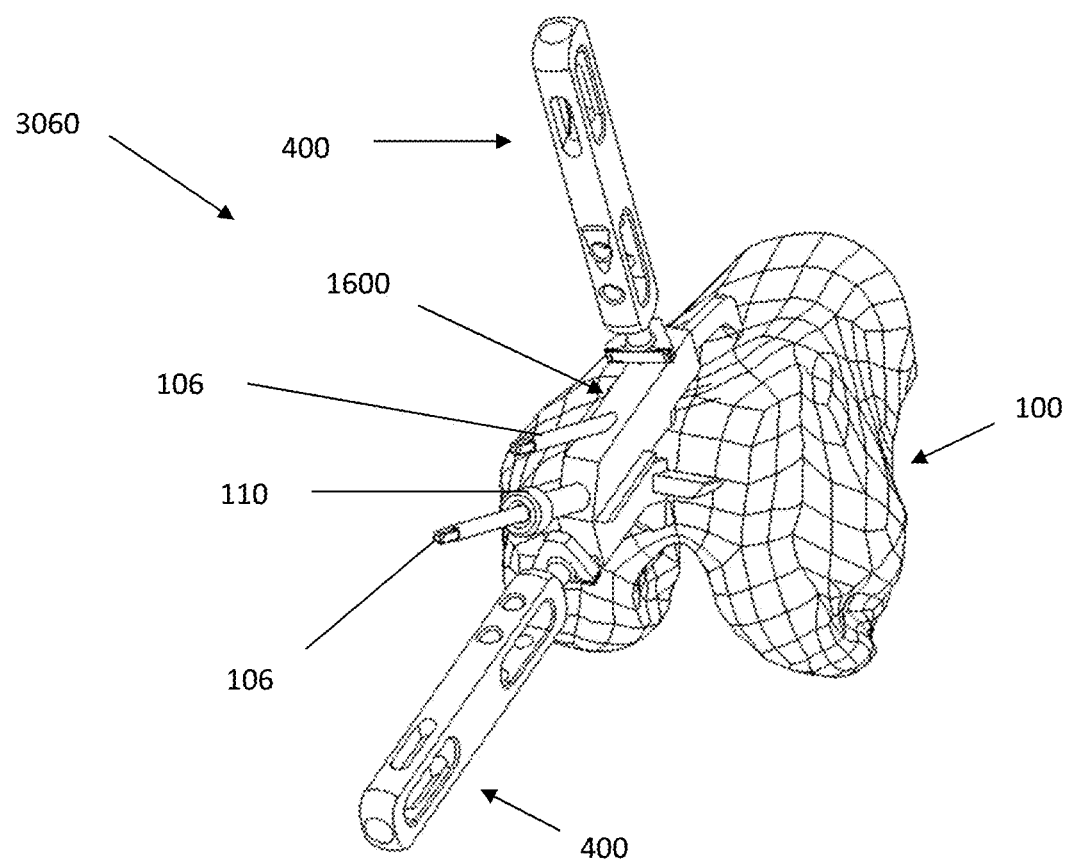
FIG. 27 shows a perspective view of a sizing and punning step and a trochlear trajectory assembly having a monolithic trochlear trajectory finder ("TTF").

The monolithic TTF 1600 may be used as an alternative trochlear referencing scheme where sizing is the initial step. Further, the monolithic TTF 1600 is right and left knee specific with the wings of the monolithic TTF representing the widest M-L aspect of a trochlear region of a patellofemoral implant. FIG. 27 shows a sizing and pin insertion step. Alignment handles 400 are placed in the first and second alignment holes 1606, 1610. The monolithic TTF 1600 is placed onto the femur bone 100 with the stylus tip 1618 planarly contacting the anterior cortex just proximal of the trochlear groove, and the posterior projection 1626 placed along the trochlear groove. The surgeon rotationally aligns the monolithic TTF 1600 using the wings 1620 as a visual reference to represent the lateral and medial width of a corresponding patellofemoral implant. Once the surgeon determines the proper orientation and size, the spiked sleeve 110 is inserted into the first reference pinhole 1606. Spikes at the end of the spiked sleeve 110 are impacted into the femur bone 100 to provide stability to the monolithic TTF 1600 while the surgeon inserts reference pins 106 through a passageway in the spiked sleeve 110 and into the second reference pinhole 1610. Once the reference pins 106 are inserted, the spiked sleeve 110 and monolithic TTF 1600 are removed from the femur bone 100, while the first and second reference pin 1606, 1610 remain.

The most distal reference pin 106 may be used as reference for the reamer 900 as previously described to form a bone void. Anterior resection may then be performed by utilizing a captured resection guide 1700. Alternatively, the trochlear punch assembly 3040 may be utilized to punch the femur bone 100 prior to anterior resection.

Figure 30:
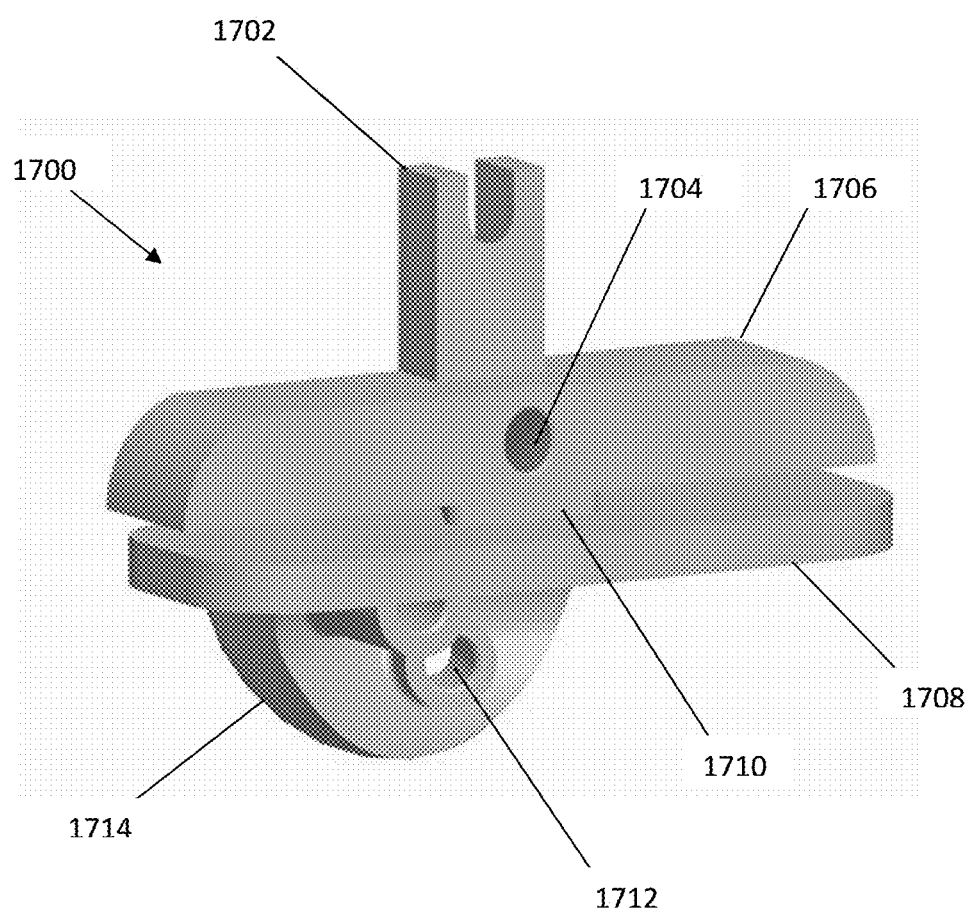
FIG. 30 shows a perspective view of a captured resection guide.

FIG. 30 shows the captured resection guide 1700. The captured resection guide 1700 generally includes a resection plate 1708, a restriction plate 1706, a central post 1710, a cylindrical portion 1714, alignment pinholes 1704, and cross pinholes 1712. The diameter of the cylindrical portion 1714 is determined by the diameter of the bone void formed by the reamer 900. An alignment pinhole 1704 extends through the center of the cylindrical portion 1714 for reference to the most distal reference pin 106 located by the monolithic TTF 1700. The cylindrical portion 1714 also has cross pinholes 1712 that extend through the cylindrical portion 1714 at an oblique angle in order to provide added stability to the captured resection guide 1700 during resection. The resection and restriction plates 1708, 1706 are attached to the face of the cylindrical portion 1714. The resection plate 1708 and restriction plate 1706 are connected by a central post 1710 that may be triangular to provide enhanced cutting angles. The restriction plate 1706 has an alignment pinhole 1704 extending therein for reference to the proximal most reference pin 106 located by the monolithic TTF 1700.

An anterior resection step may be performed by placing the alignment pinhole 1710 of the cylindrical portion over the distal most reference pin 106 and the alignment pinhole 1704 of the restriction plate over the proximal most reference pin 106, thus providing rotational and anatomical alignment. The cylindrical portion 1714 is then inserted into the bone void formed by the reamer 900. The resection plane may be optionally demonstrated by the blade runner 700 as previously described. A bone saw is then used to resect the femur bone anteriorly through the gap between the restriction and resection plates 1706, 1708. The captured resection guide 1700 may be removed from the reference pins 106 to prepare for further bone preparation steps. Alternatively, the captured resection guide 1700 and reference pins 106 may be removed from the femur bone 100 for implantation of a circular rim implant.

Figure 31A:
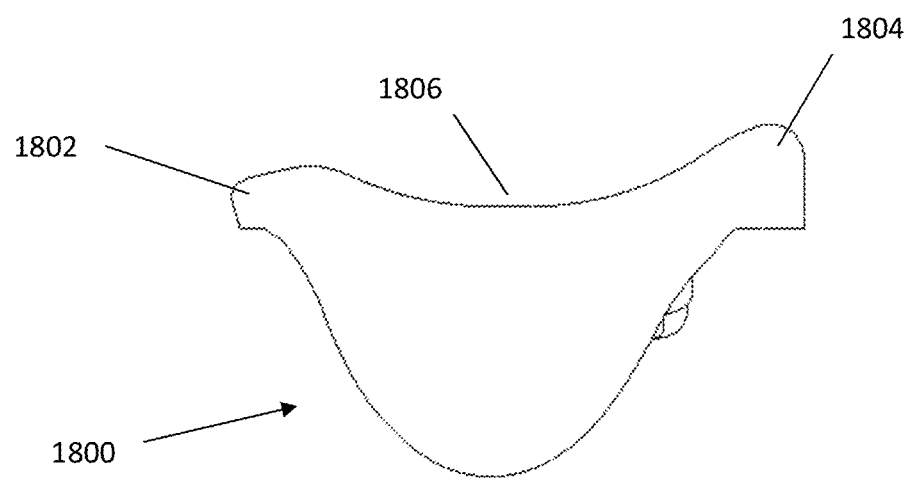
FIG. 31A shows a front view of an embodiment of an articular surface of a patellofemoral implant.
Figure 31B:
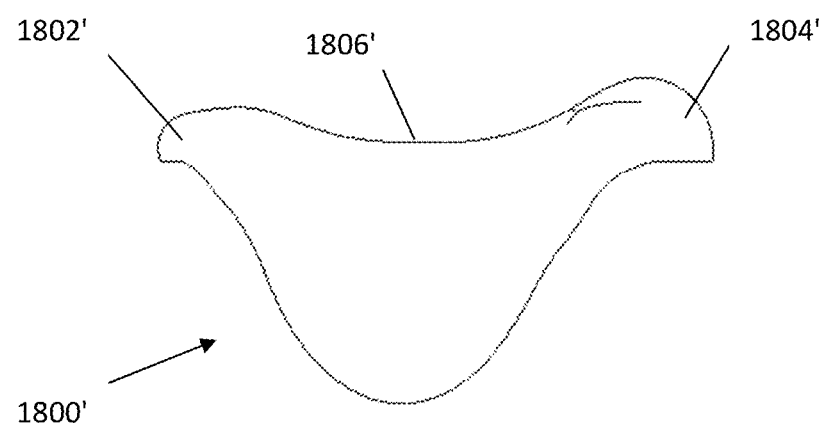
FIG. 31B shows a front view of another embodiment of an articular surface of a patellofemoral implant.

FIGS. 31A-34D show various embodiments of a patellofemoral implant. These embodiments are merely exemplary and are not meant to be exhaustive of the possible variations. The patellofemoral implant generally includes an articular surface 1800, a bone contact surface 1900, a distal region 1910, and a proximal region 1908. The articular contact surface generally includes a lateral flange 1804 and a medial flange 1802. The intersection of the lateral and medial flange 1804, 1802 forms a trochlear region 1806. The lateral flange 1804 sits prouder than the medial flange 1802 in order to prevent patellar subluxation and to more closely conform to the contours of the natural knee for improved patellar tracking and to maintain the natural Q-angle. This enhanced geometry is such that the patellofemoral implant is left and right leg specific. FIG. 31A shows an embodiment of the articular surface 1800 of the patellofemoral implant where the medial and lateral flange 1802, 1804 have a steep drop to the resection level from an apex of the medial and lateral flange 1802, 1804. FIG. 31B shows another embodiment of the articular surface 1800' where the lateral flange 1804' and medial flange 1802' tapers down to the resection level for a gradual transition to cartilage.

The bone contact surface 1900 generally includes a plurality of protrusions extending outwardly from the bone contact surface 1900 for insertion into bone voids formed in the femur bone 100. The plurality of protrusions may include pegs 1916, 1922 a closed circular rim 1912, an open circular rim 1918 or any combination thereof.

FIGS. 32A-34D show a preferred embodiment of the proximal region 1908, wherein the protrusions are three pegs 1916 extending from the bone contact surface 1900 of the proximal region 1908. While three pegs 1916 are shown, one or two pegs 1916 may also be utilized. The pegs 1916 preferably extend from the bone contact 1900 surface of the proximal region 1908 at a 45 degree angle with respect to the bone contact surface 1900 in order to guide the patellofemoral implant into its desired location during implantation. However, peg angles from 15-60 degrees may also be utilized. The locations of the pegs 1916 are optimized for density and implant liftoff resistance. Each peg 1916 is preferably the same length, however, peg lengths may vary to be within 30% of each other.

FIGS. 32A-32D show one embodiment of a closed circular rim 1912 embodiment of the distal region 1910. The closed circular rim 1912 is annular to form a cavity 1914 within the circular rim. The circular rim provides a greater contact area between the patellofemoral implant, bone cement, and bone to aid in fixation. Further, the circular nature of the closed circular rim 1912 inhibits the formation of hazardous stress concentrations.

Figure 33A:
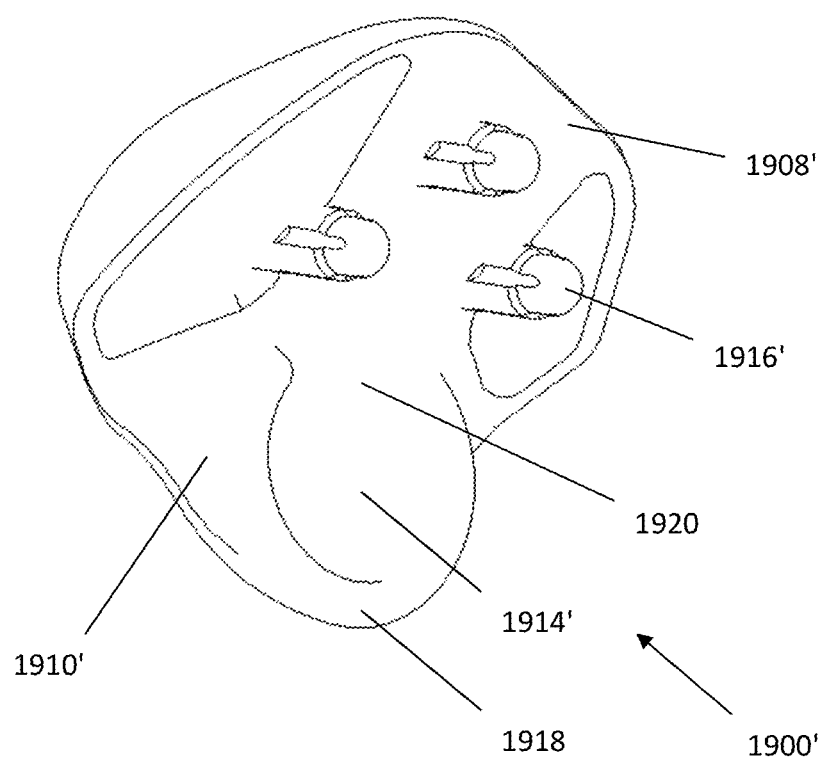
FIG. 33A shows a perspective view of an open circular rim embodiment of a bone interface surface of one embodiment of a patellofemoral implant.
Figure 33B:
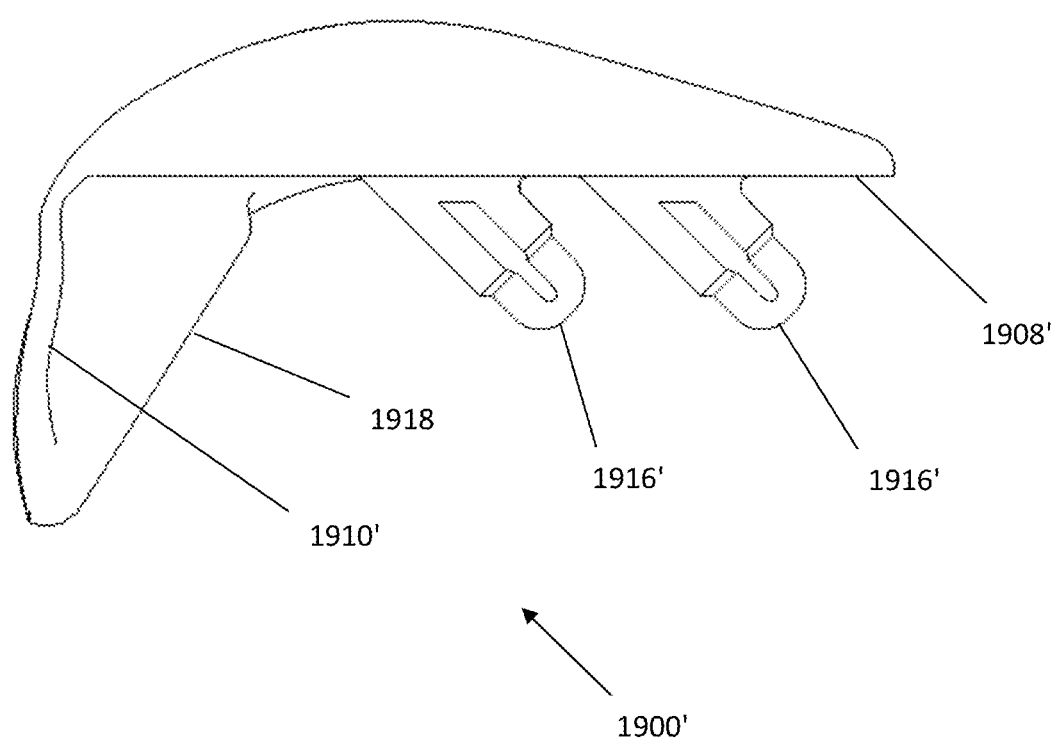
FIG. 33B shows a side view of the patellofemoral implant of FIG. 33A.
Figure 33C:
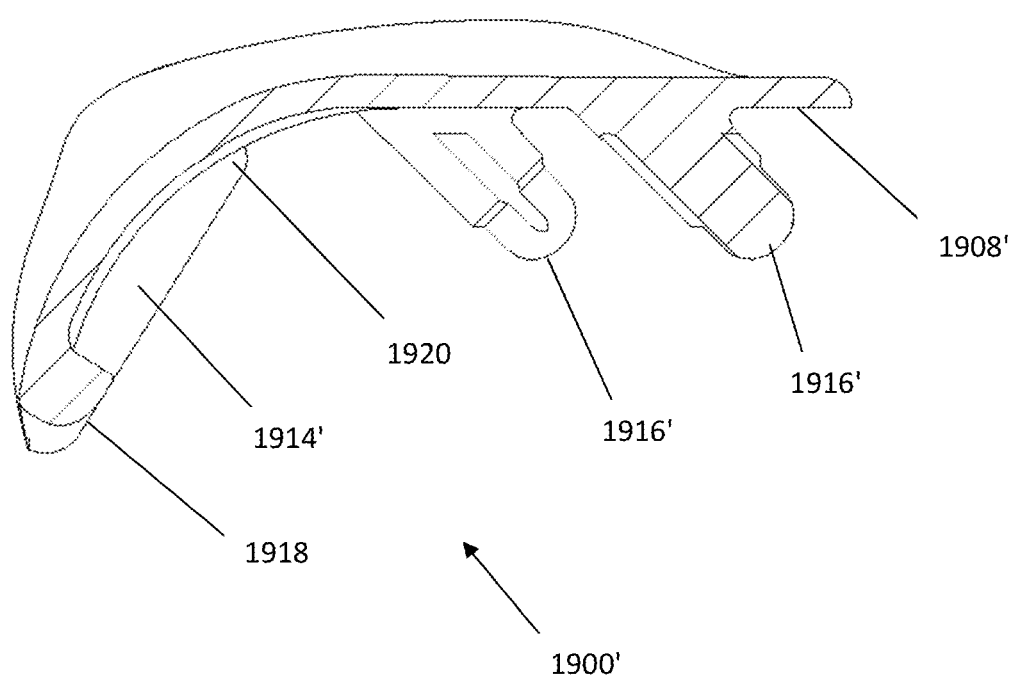
FIG. 33C shows a cross-sectional view of the patellofemoral implant of FIG. 33A.
Figure 33D:
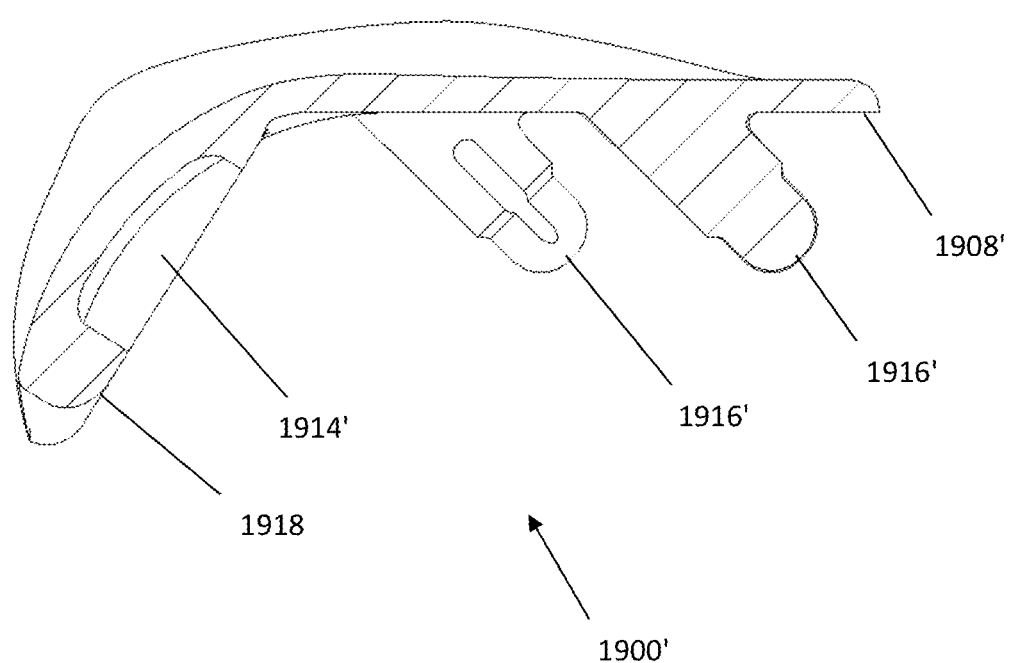
FIG. 33D shows another cross-sectional view of the patellofemoral implant of FIG. 33A.
Figure 34A:
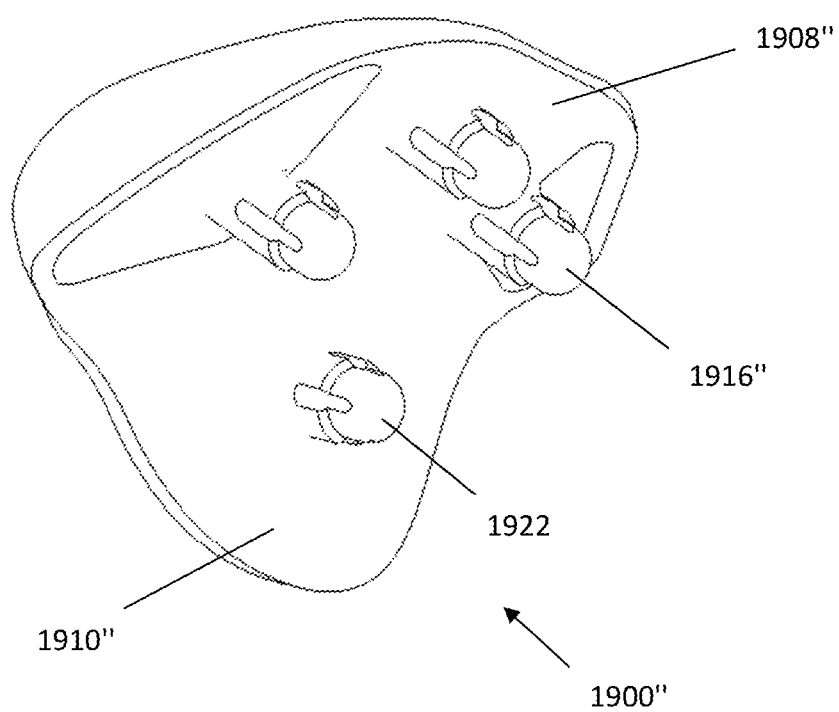
FIG. 34A shows a rimless embodiment of a bone interface surface of a patellofemoral implant.
Figure 34B:
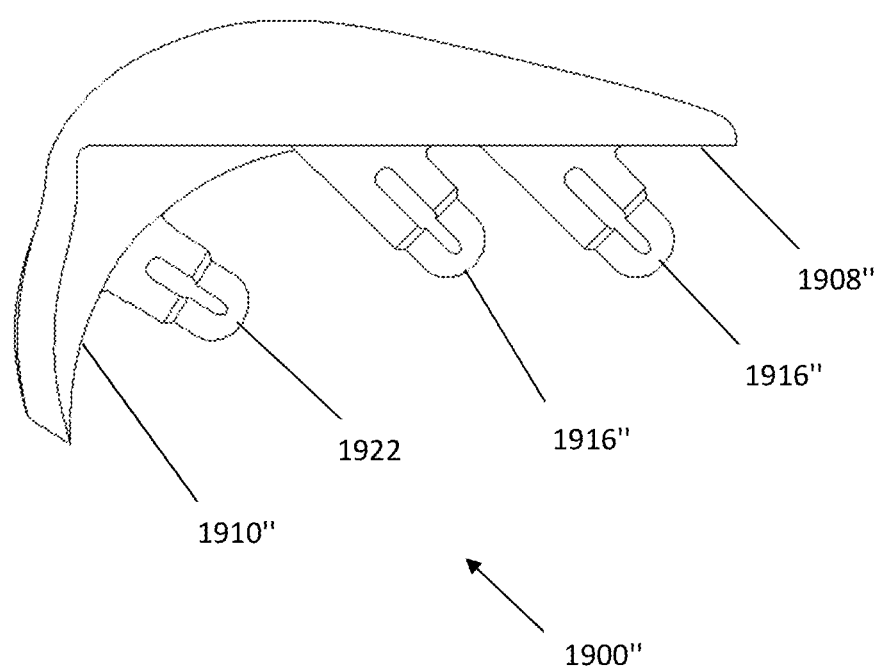
FIG. 34B shows a side view of the patellofemoral implant of FIG. 34A.
Figure 34C:
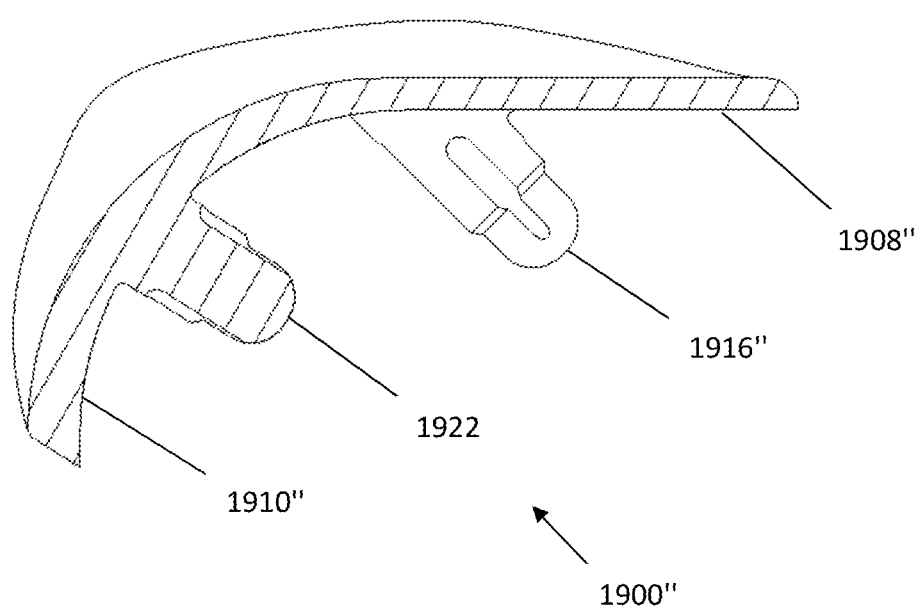
FIG. 34C shows a cross-sectional view of the patellofemoral implant of FIG. 34A.
Figure 34D:
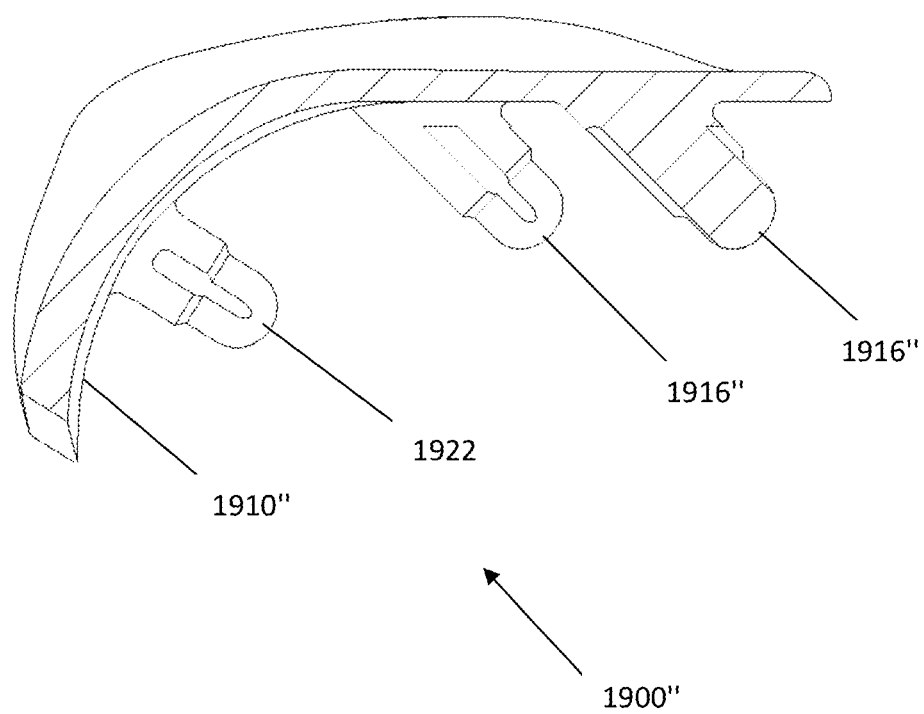
FIG. 34D shows another cross-sectional view of the patellofemoral implant of FIG. 34A.

FIGS. 33A-33D show one embodiment of an open circular rim 1918 embodiment of the distal region 1910'. The open circular rim 1918 is an annular feature that extends from the bone contact surface 1900' of the distal region 1910' and is similar to the closed circular rim 1912 with the exception of a cut-out 1920 in the open circular rim 1918. This cut-out 1920 may face the proximal region 1908' as shown in FIGS. 33A and 33C. However, the cut-out 1920 may also be a plurality of cut-outs that are radially arrayed around the circumference of the open circular rim 1918 (not shown). The cut-out 1920 allows bone cement to flow out of the open circular rim 1918 once filled to ensure that the bone cement can properly pressurize.

Figure 32A:
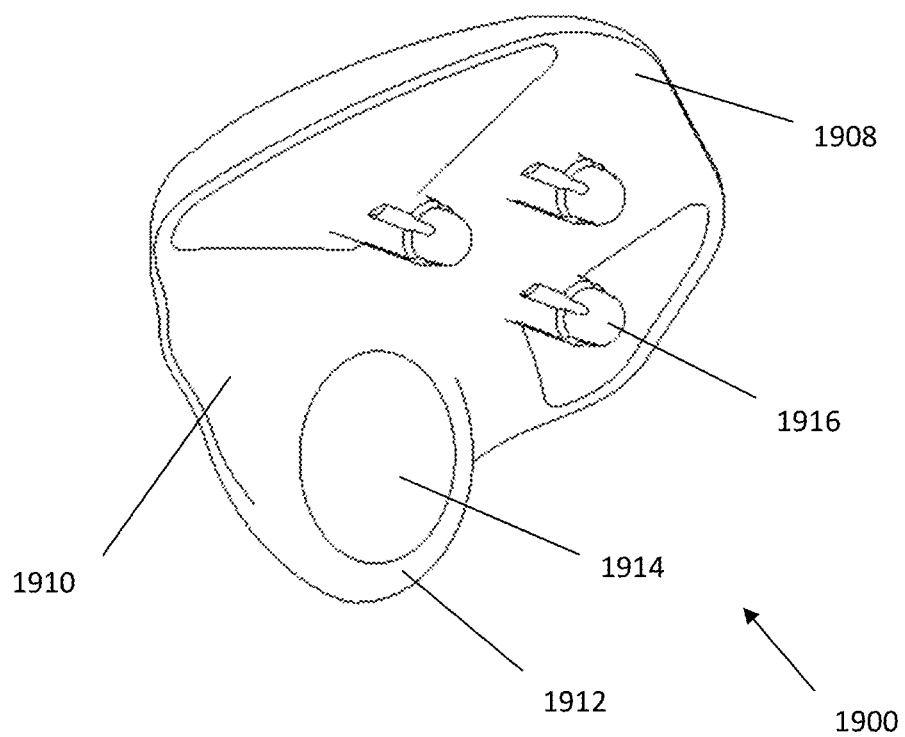
FIG. 32A shows a perspective view of closed circular rim embodiment of a bone interface surface of a patellofemoral implant.
Figure 32B:
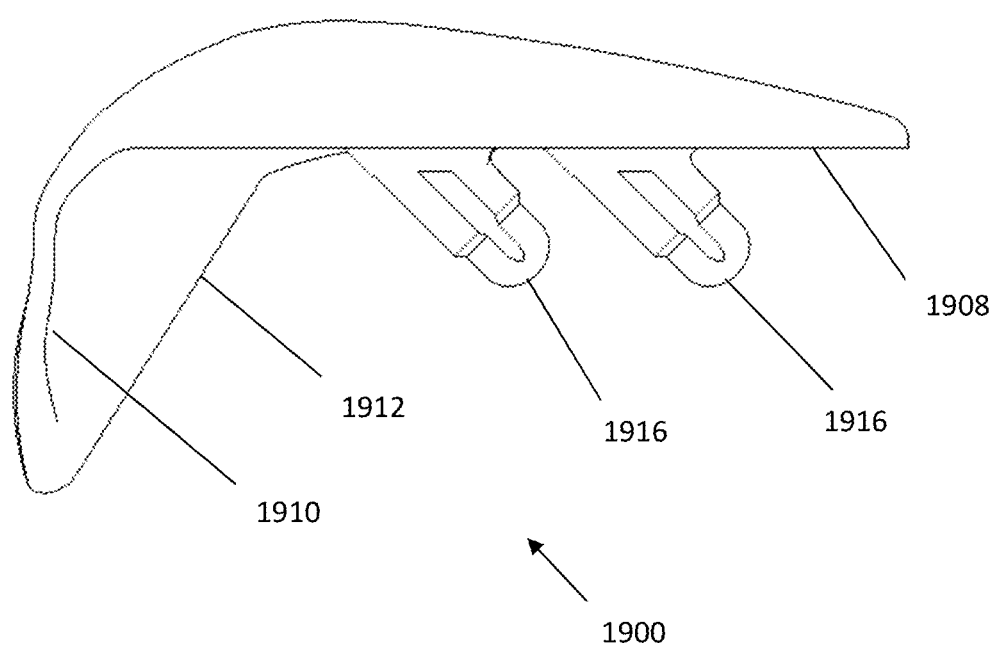
FIG. 32B shows a side view of the patellofemoral implant of FIG. 32A.
Figure 32C:
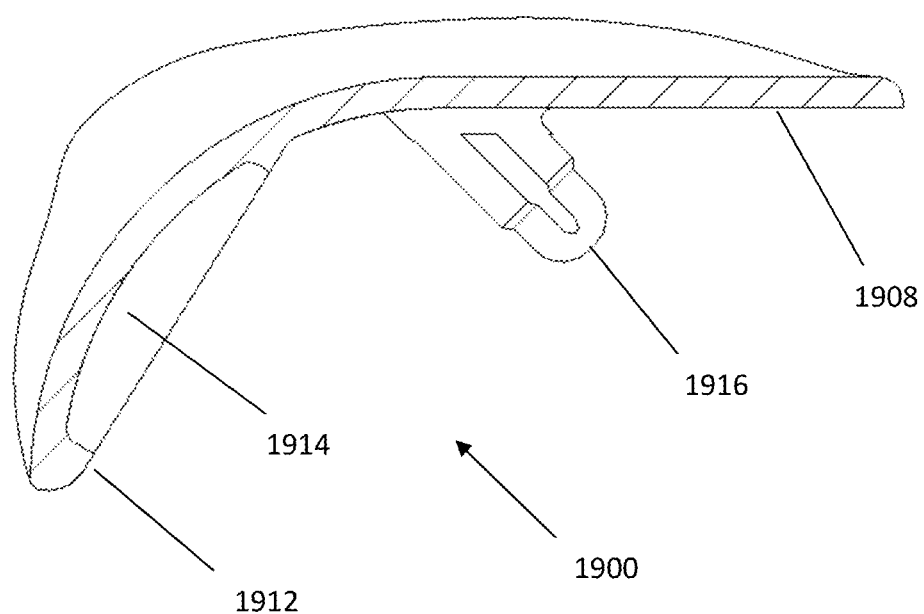
FIG. 32C shows a cross-sectional view of the patellofemoral implant of FIG. 32A.
Figure 32D:
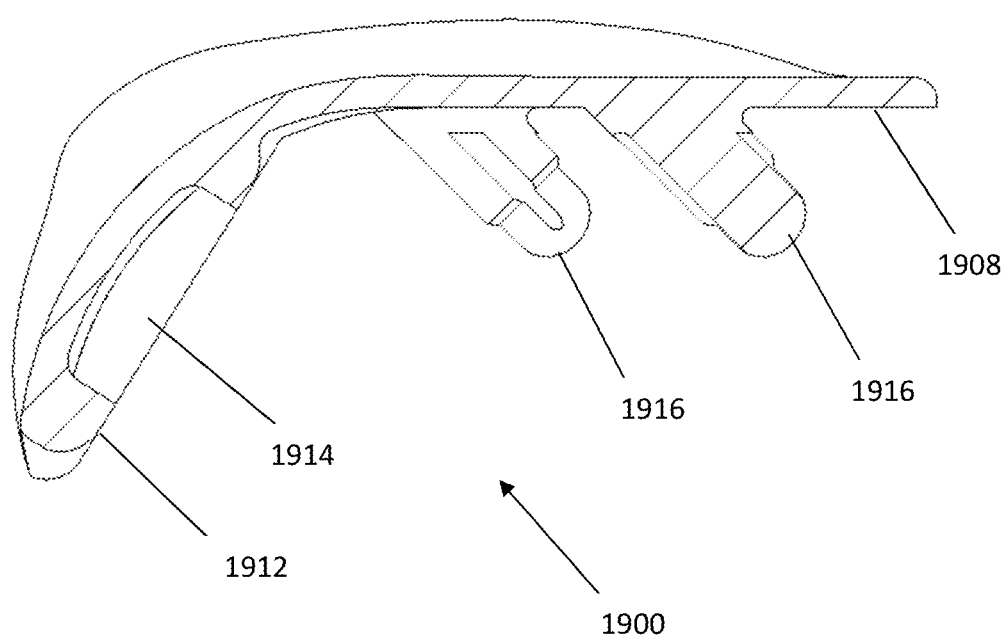
FIG. 32D shows another cross-sectional view of the patellofemoral implant of FIG. 32A.

FIGS. 34A-34D show a rimless embodiment of the distal region 1910". Rather than a rim, a peg 1922 extends from the bone contact surface 1900" of the distal region 1910". The peg 1922 provides further stability and fixation while retaining a majority of the cortical bone in the trochlear region. The peg 1922 is preferably centered about the saggital radius arc length as seen in FIGS. 32B-32D. However, it may be offset from the center point of the sagittal radius arc by about plus/minus 20 degrees.

The patellofemoral implant may be provided in a multitude of sizes, for example each embodiment described herein may be provided in four or more sizes, which are left and right leg specific, for a total of at least eight patellofemoral implants per embodiment.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for replacing a trochlear groove region of a femur bone, comprising:

a prosthesis having a bone contact surface and a prosthesis periphery defining an outer perimeter of the bone contact surface; and a first template having a proximal portion, a distal extension, a lateral extension, and a medial extension, the proximal portion having a first bone contact surface having a first outer perimeter, the distal extension extending from the proximal portion and terminating at a distal extent, the lateral extension extending from the distal extension and terminating at a lateral extent, and the medial extension extending from the distal extension and terminating at a medial extent, wherein the distal, lateral, and medial extents are discontinuous with one another, and wherein at least a portion of the first outer perimeter and the distal, lateral, and medial extents define a first template periphery that substantially corresponds to the prosthesis periphery.

2. The system of claim 1, wherein the first bone contact surface is substantially planar for engaging a resected portion of the femur bone, and the proximal portion includes a viewing window extending therethrough for viewing the engagement of the first bone contact surface with the resected portion of the femur bone.

3. The system of claim 1, wherein the distal extension is arcuate and tapers inwardly from the proximal portion to the distal extent, the distal extension including a bossed pinhole extending therethrough, and the medial and lateral extension are connected to a boss of the bossed pinhole and extend therefrom.

4. The system of claim 1, wherein the lateral extension is a lateral wing and the medial extension is a medial wing, the lateral wing tapers from the distal extension to the lateral extent forming a lateral bone contact tip at the lateral extent, and the medial wing tapers from the distal extension to the medial extent forming a medial bone contact tip at the medial extent.

5. The system of claim 4, wherein the lateral and medial bone contact tips are each capped by a bone contact sphere.

6. The system of claim 1, wherein the bone contact surface of the prosthesis includes an annulus projecting outwardly therefrom for insertion into a bone void formed in the femur bone, the annulus having a sidewall defining a cavity therein.

7. The system of claim 1, further comprising a second template having a second bone contact surface and a second template periphery substantially corresponding to the prosthesis periphery, the second bone contact surface having a plurality of guide holes extending therethrough and an annulus projecting outwardly therefrom for insertion into a bone void formed into the femur bone.

8. The system of claim 7, wherein the second bone contact surface includes flanges extending therefrom along the second template periphery for insertion into a resected portion of the femur bone.

9. A system for replacing a trochlear groove region of a femur bone, comprising:

a prosthesis having a bone contact surface disposed opposite an articular surface thereof and a prosthesis periphery defining an outer perimeter of the bone contact surface, the bone contact surface having an annulus projecting outwardly therefrom for insertion into a bone void formed in the femur bone, the annulus having a sidewall and a base surface intersecting the sidewall, the sidewall having a first end connected to the bone contacting surface and extending therefrom to a second end, the base surface and sidewall defining a recess for receipt of bone cement therein, the base surface being closed and defining a bottom of the recess, the second end of the sidewall being positioned further from the articular surface than the base surface and defining an opening to the recess that opens in a direction away from the articular surface; and a first template having a first bone contact surface and a first template periphery that substantially corresponds to the prosthesis periphery, the first bone contact surface having a plurality of guide holes extending therethrough and a first annulus projecting outwardly therefrom for insertion into the bone void.

10. The system of claim 9, further comprising a second template having a proximal portion, a distal extension, a lateral extension, and a medial extension, the proximal portion having a second bone contact surface having a second outer perimeter, the distal extension extending from the proximal portion and terminating at a distal extent, the lateral extension extending from the distal extension and terminating at a lateral extent, and the medial extension extending from the distal extension and terminating at a medial extent.

* * * * *